(12) United States Patent
Mangum et al.

(10) Patent No.: US 8,769,438 B2
(45) Date of Patent: Jul. 1, 2014

(54) METHODS AND SYSTEM FOR DISPLAYING PEDIGREE CHARTS ON A TOUCH DEVICE

(75) Inventors: Gary Mangum, Springville, UT (US); Josh Bryant, Bend, OR (US)

(73) Assignee: Ancestry.com Operations Inc., Provo, UT (US)

( * ) Notice: Subject to any disclaimer, the term of this patent is extended or adjusted under 35 U.S.C. 154(b) by 19 days.

(21) Appl. No.: 13/333,670

(22) Filed: Dec. 21, 2011

(65) Prior Publication Data

US 2013/0167088 A1  Jun. 27, 2013

(51) Int. Cl.
*G06F 3/048* (2013.01)
*G06F 3/0488* (2013.01)
*G06F 3/0485* (2013.01)
*G06F 3/0486* (2013.01)
*G06F 17/30* (2006.01)
*G06Q 10/06* (2012.01)
*G06F 19/26* (2011.01)

(52) U.S. Cl.
CPC ............ *G06F 3/0488* (2013.01); *G06F 3/0485* (2013.01); *G06F 3/0486* (2013.01); *G06F 17/30961* (2013.01); *G06Q 10/06* (2013.01); *G06F 19/26* (2013.01); *G06F 2203/04803* (2013.01)
USPC ........... 715/853; 715/784; 715/786; 715/792; 715/799; 715/854; 715/863

(58) Field of Classification Search
CPC . G06F 3/0488; G06F 3/0485; G06F 3/04886; G06F 17/30961; G06F 19/26; G06F 2203/04803; G06Q 10/06
USPC .......... 715/815, 784, 853, 854, 863, 792, 799
See application file for complete search history.

(56) References Cited

U.S. PATENT DOCUMENTS

| | | | | |
|---|---|---|---|---|
| 6,373,488 B1* | 4/2002 | Gasper et al. | ................. | 345/427 |
| 6,436,204 B1* | 8/2002 | Gates et al. | ................... | 148/527 |
| 6,570,567 B1* | 5/2003 | Eaton | ............................ | 345/428 |
| 7,257,776 B2* | 8/2007 | Bailey et al. | .................. | 715/788 |
| 7,791,770 B2 | 9/2010 | Nomura | | |
| 8,224,862 B2* | 7/2012 | Sacks | ............................ | 707/797 |
| 2001/0054089 A1 | 12/2001 | Tso et al. | | |
| 2002/0145631 A1* | 10/2002 | Arbab et al. | .................. | 345/786 |
| 2003/0193481 A1* | 10/2003 | Sokolsky | ....................... | 345/173 |

(Continued)

FOREIGN PATENT DOCUMENTS

JP  2005304308 A  * 11/2005

*Primary Examiner* — Patrick Riegler
*Assistant Examiner* — Nicholas Klicos
(74) *Attorney, Agent, or Firm* — Kilpatrick Townsend & Stockton LLP

(57) ABSTRACT

The present invention discloses an air fan turbine positioned horizontally or vertically in close proximity to the exhaust fan system of air handler systems. These turbine units catch the exhausted air flow from the exhaust ports of these air handler units to drive the turbine blades which are attached to a generator. As the propellor blades spin, they generate electricity. Thus, the man made air flow known as exhaust from the air handler systems is used to produce electricity. This invention not only uses man made air flow, but also repositions the air turbine 90° from a horizontal position to a vertical position to receive wind air from the atmosphere. When the air handler unit is turned off, a signal is sent to mechanically move the air turbine to the vertical position to redirect itself to then catch natural wind airflow on both roof top and ground mounted units.

19 Claims, 11 Drawing Sheets

(56) References Cited

U.S. PATENT DOCUMENTS

| | | | |
|---|---|---|---|
| 2004/0090462 A1* | 5/2004 | Graham ........................ 345/767 |
| 2006/0020970 A1* | 1/2006 | Utsuki et al. .................... 725/39 |
| 2006/0059435 A1* | 3/2006 | Molesky et al. ............. 715/786 |
| 2006/0242603 A1* | 10/2006 | Wong et al. .................... 715/853 |
| 2008/0168357 A1 | 7/2008 | Firebaugh et al. |
| 2008/0222558 A1* | 9/2008 | Cho et al. ...................... 715/784 |
| 2008/0288886 A1 | 11/2008 | Sherwood et al. |
| 2009/0031239 A1 | 1/2009 | Coleran et al. |
| 2009/0152349 A1* | 6/2009 | Bonev et al. .................. 235/383 |
| 2009/0172603 A1 | 7/2009 | Young Suk Lee |
| 2009/0198725 A1* | 8/2009 | Lee et al. ...................... 707/102 |
| 2009/0249257 A1* | 10/2009 | Bove et al. .................... 715/858 |
| 2009/0292989 A1* | 11/2009 | Matthews et al. ............. 715/702 |
| 2010/0083173 A1* | 4/2010 | Germann et al. ............. 715/810 |
| 2010/0131886 A1* | 5/2010 | Gannon et al. ................ 715/786 |
| 2010/0185949 A1* | 7/2010 | Jaeger ........................... 715/730 |
| 2010/0199222 A1* | 8/2010 | Kranik et al. ................. 715/853 |
| 2010/0251165 A1* | 9/2010 | Williams ...................... 715/784 |
| 2010/0287154 A1* | 11/2010 | Tee et al. ....................... 707/708 |
| 2011/0072009 A1* | 3/2011 | Tuttle et al. ................... 707/722 |
| 2011/0148878 A1 | 6/2011 | Baikie |
| 2011/0161805 A1* | 6/2011 | Slinker ......................... 715/245 |
| 2011/0231796 A1* | 9/2011 | Vigil ............................. 715/810 |
| 2012/0054190 A1* | 3/2012 | Peters ........................... 707/741 |
| 2012/0062564 A1* | 3/2012 | Miyashita et al. ............ 345/419 |
| 2013/0007671 A1* | 1/2013 | Hammontree et al. ....... 715/853 |
| 2013/0124528 A1* | 5/2013 | Gourdol et al. ............... 707/740 |

* cited by examiner

METHODS AND SYSTEM FOR DISPLAYING PEDIGREE CHARTS ON A TOUCH DEVICE

CROSS-REFERENCES TO RELATED APPLICATIONS

This application is related to U.S. patent application Ser. No. 13/035,845 filed on Feb. 25, 2011 entitled "ANCESTOR-TO-ANCESTOR RELATIONSHIP LINKING METHODS AND SYSTEMS" which is incorporated herein by reference. This application is also related to co-pending U.S. patent application Ser. No. 13/035,816 filed on Feb. 25, 2011 entitled "METHODS AND SYSTEMS FOR IMPLEMENTING ANCESTRAL RELATIONSHIP GRAPHICAL INTERFACE" which is also incorporated herein by reference.

TECHNICAL FIELD

The present invention relates generally to methods and systems for displaying genealogical records on a touch-screen device and more specifically to methods and systems for transitioning between displayed records and/or between one or more views.

BACKGROUND OF THE INVENTION

Interest in genealogical research has grown tremendously over the last century and has become a popular hobby among all age groups. Much of the excitement surrounding genealogy stems from a researcher's ability to study the various relationships within their family trees—to see who they are related to and how. When a researcher discovers that they are in some way related to another individual, it is common for the researcher to desire to understand the exact nature of that relationship.

Genealogical records often include relationship information that identifies how records and sub-records are related or connected. These records may include other information as well, such as date of birth, date of death, date of marriage, city and/or state of residence, spouse information, children information, etc. However, only a limited amount of this information may be displayed on a touch-screen device at one time It is often desired and/or important to visually display how genealogical records and/or sub-records are linked or related (i.e., display the connections between records). For example, it may be helpful to display an individual's ancestors so that users can visually determine how the individual is connected or interconnected with other individuals in a genealogical chart. Showing the connectedness of other records may likewise be important, such as the connection between different types of family relationships, such as sibling, parent, child, cousin, etc. Because of the usefulness of such displays, there is a need in the art for improved ways to display and navigate genealogical records.

BRIEF SUMMARY OF THE INVENTION

In one embodiment, a method for navigating between a plurality of genealogical records displayed on a touch-screen device is discussed. The method includes receiving a selection of a first genealogical record in the plurality of genealogical records and determining a plurality of familial records in the plurality of genealogical records that are related to the first genealogical record through one or more familial lines. The method further includes determining a first display group comprised of the first genealogical record and a familial record in each familial line, and determining a second display group comprised of a second familial record in a first familial line, wherein the second familial record in the second display group sequentially follows a familial record in the first display group. The method also includes causing to be displayed on a touch screen of the touch-screen device, a first plurality of icons representing each familial record in the first display group, where each icon in the first plurality of icons is positioned according to the one or more familial lines such that each familial line forms a familial line direction. Additionally, the method includes determining a direction from a finger gesture input from the touch screen of the touch-screen device, and determining that the first familial line corresponds to the direction of the finger gesture input. The method further includes adding to the first display group, the second familial record from the second display group, and adding to the second display group, a third familial record in the first familial line that follows after the second familial record in the second display group. The method also includes causing to be displayed on the touch screen of the touch-screen device, an icon representing the second familial record added to the first display group.

In another embodiment, a system for displaying and navigating between a plurality of genealogical records is discussed. The system may include a processor, a touch screen; and a storage memory coupled with the processor. The storage memory may include a set of instructions stored thereon which, when executed by the processor, cause the processor to store the plurality of genealogical records and receive a selection of a first genealogical record in the plurality of genealogical records. The instructions may further cause the processor to determine a plurality of familial records in the plurality of genealogical records that are related to the first genealogical record through one or more familial lines, and determine a first display group comprised of the first genealogical record and a familial record in each familial line. The instructions may also cause the processor to determine a second display group comprised of a second familial record in a first familial line, wherein the second familial record in the second display group sequentially follows a familial record in the first display group. The instructions may additionally cause the processor to cause to be displayed on the touch screen, a first plurality of icons representing each familial record in the first display group, wherein each icon in the first plurality of icons is positioned according to the familial lines such that each familial line forms a familial line direction. Moreover, the instructions may cause the processor to determine a direction from a finger gesture input from the touch screen, and determine that the first familial line corresponds to the direction of the finger gesture input. The instructions may further cause the processor to add to the first display group, the second familial record from the second display group, and add to the second display group, a third familial record in the first familial line that follows after the second familial record in the second display group. The instructions may also cause the processor to cause to be displayed on the touch screen of the touch screen, an icon representing the second familial record added to the first display group.

In another embodiment, a non-transitory computer-readable medium is discussed. The medium may include a set of instructions stored thereon, which when executed by a computer, cause the computer to store the plurality of genealogical records and receive a selection of a first genealogical record in the plurality of genealogical records. The instructions may further cause the computer to determine a plurality of familial records in the plurality of genealogical records that are related to the first genealogical record through one or more familial lines and determine a first display group comprised of the first genealogical record and a familial record in each familial line. The instructions may also cause the computer to determine a second display group comprised of a second familial record in a first familial line, wherein the second familial record in the second display group sequentially follows a familial record in the first display group. The instructions may additionally cause the computer to cause to be displayed on a touch screen, a first plurality of icons representing each familial record in the first display group, wherein each icon in the first plurality of icons is positioned according to the familial lines such that each familial line forms a familial line direction. Moreover, the instructions may cause the computer to determine a direction from a finger gesture input from the touch screen, and determine that the first familial line corresponds to the direction of the finger gesture input. The instructions may further cause the computer to add to the first display group, the second familial record from the second display group, and add to the second display group, a third familial record in the first familial line that follows after the second familial record in the second display group. The instructions may also cause the computer to cause to be displayed on the touch screen, an icon representing the second familial record added to the first display group.

BRIEF DESCRIPTION OF THE DRAWINGS

A further understanding of the nature and advantages of the present invention may be realized by reference to the following drawings. In the appended figures, similar components or features may have the same reference label. Further, various components of the same type may be distinguished by following the reference label by a second label that distinguishes among the similar components.

DETAILED DESCRIPTION OF THE INVENTION

While various aspects and features of certain embodiments have been summarized above, the following detailed description illustrates a few exemplary embodiments in further detail to enable one of skill in the art to practice such embodiments. In the following description, for the purposes of explanation, numerous specific details are set forth in order to provide a thorough understanding of the described embodiments. It will be apparent, however, to one skilled in the art that other embodiments of the present invention may be practiced without some of these specific details. In other instances, well-known structures and devices are shown in block diagram form. Several embodiments are described herein, and while various features are ascribed to different embodiments, it should be appreciated that the features described with respect to one embodiment may be incorporated into other embodiments as well. By the same token, however, no single feature or features of any described embodiment should be considered essential to every embodiment of the invention, as other embodiments of the invention may omit such features.

A set of embodiments provides solutions (including without limitation, devices, systems, methods, software programs, and the like) for implementing a method for the interactive display of familial relationships on a touch-screen device. Instead of displaying only a textual description of how two individuals in a genealogical tree are related to each other, aspects of the present invention improve the prior art by causing to be graphically displayed a view of the connecting relationships for each level in a generational hierarchy comprised of various familial lines. Navigation along the familial lines may be accomplished by using various finger gestures on the touch-screen device that provide directional information that align with a direction of various relationship pathways.

Figure 1:
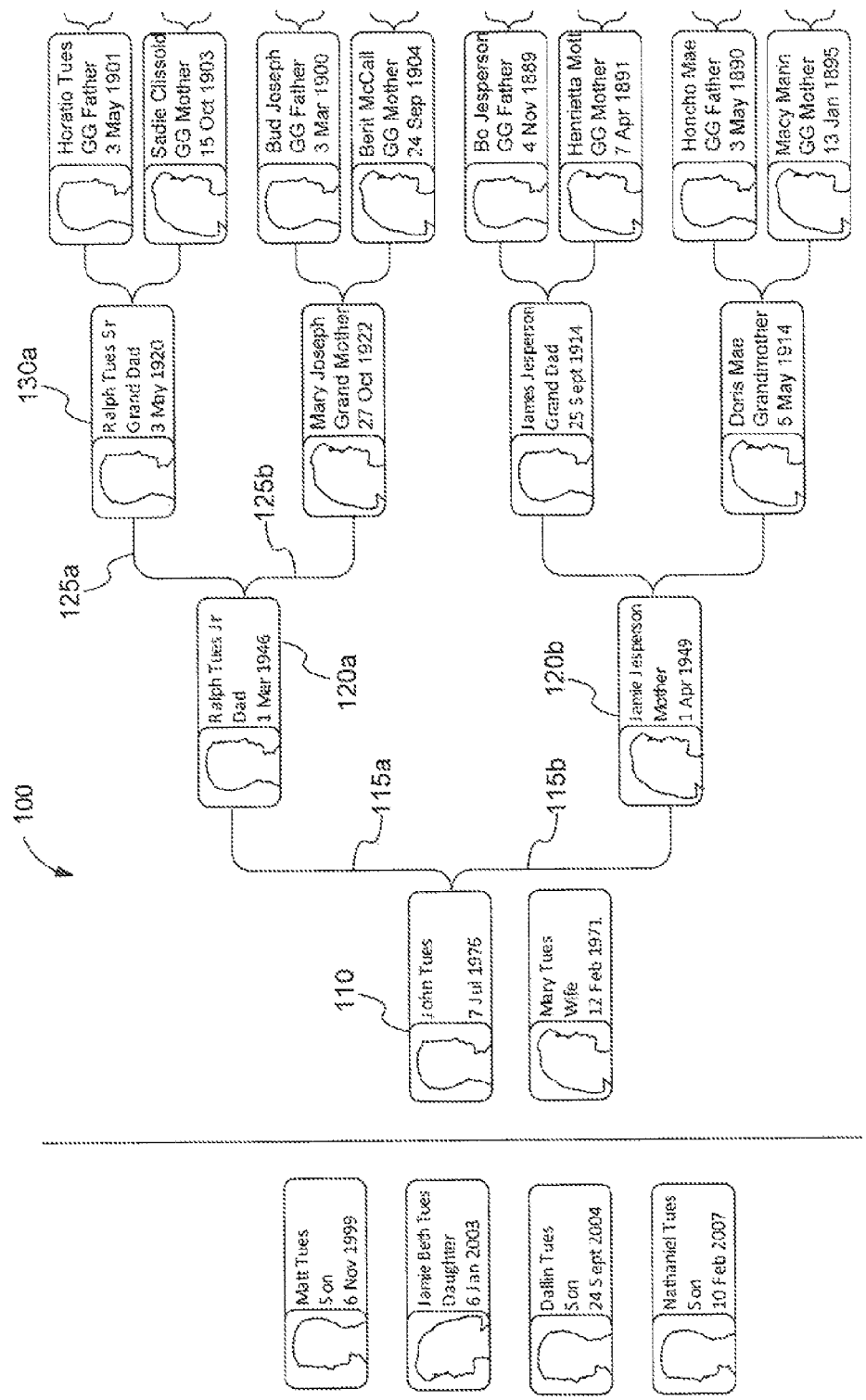
FIG. 1 is an embodiment of a genealogical chart that may be used to record family relationships.

To begin, family relationships for genealogical research may be stored and displayed in one or more genealogical charts. FIG. 1 illustrates an embodiment of a chart 100 that may be used to display family relationships. Genealogical charts representing family trees may be displayed on the screen of a computer system. Each node in the chart represents a person within a family, and a set of lines connecting the nodes may represent family relationships that connect the various family members to each other within the family structure. Such relationships may consist of sibling, parent, or child relationships, and/or the like. By way of example, node 110 represents a single family member, and relationship 115a represents a parent-child relationship between the parent node 120a and a child node 110.

The view of the genealogical tree shown in FIG. 1 displays details intended to convey information regarding a particular family line. However, the number of nodes added to the family line may increase as more individuals are added to the family, increasing the number of nodes that must be simultaneously displayed if the entire family line is to be viewed at once. Consequently, a graphical representation of a genealogical chart may contain various levels or views that focus on particular subdivisions of the chart. A top-level view may depict the entire tree, and may include very few visible details related to the individual nodes. When the view is changed to the next lower level, for instance, the entire tree may no longer be visible in the display. Instead, the view may zoom in to display a group of families within the chart. In some embodiments, these may correspond to groupings of family lines. As the display zooms in to the next lower level, for instance, a family level, the display may be limited to a single family or family line, such as the line depicted in FIG. 1. Finally, the display may be zoomed in to an individual level, wherein a single individual is displayed with his/her immediate family. The individual view may also be called a "detail" view wherein all the stored information related to the individual may be displayed, such as dates, videos, documents, recordings, and/or the like. In accordance with embodiments of this invention, various methods have been developed that display an optimal amount of information for each node, while simultaneously displaying surrounding relationship information and allowing for convenient navigation around the tree.

When the user chooses to zoom to another level, such as the family view, the display may zoom within the display level (i.e. within the tree view or family view) or in some embodiments zooming in or out may cause the display to switch between views. For example, zooming in from the tree view may cause the display to transition to the family view. Zooming in further may cause the display to transition to a view focusing on a particular family line, and so forth. Zooming between levels on a touch-screen device may be accomplished through the use of finger gestures. For example, pinching or spreading two fingers in contact with the touch screen may be received as a command to zoom in or out.

In light of this disclosure, it will be understood that there are many different ways to display a genealogical chart. Many of the examples discussed herein disclose an ancestral view of a genealogical chart, wherein the display is focused on an individual, and ancestral lines are arranged to radiate away from the individual. Other views of a genealogical chart may also be used, such as a family view, a descendent view, an individual view, and/or a top-level, tree, or global view. Each of these different views may correspond to one of the detail levels discussed above, or may focus on more than one individual. Therefore, the examples used herein should be viewed as merely illustrative, and the methods for navigating through a genealogical chart are applicable to all forms of genealogical charts, displays, and views that include directional familial lines.

If the genealogical chart is being displayed on a device that accepts finger gestures as an input, these may be used to provide zoom, pan, and rotate commands for manipulating a visual representation of the genealogical chart 100. For example, on a tablet computer, e-reader, laptop computer with a pen input, and/or smart phone, it is possible to use a finger gesture such as dragging a finger across the screen to navigate around the genealogical tree. Likewise, a user could place two fingers on the screen and rotate them in order to rotate the image, or in some embodiments, to rotate around a three-dimensional tree. To zoom the image in or out, two fingers could be pinched or spread apart. These finger gestures can also be performed on a touch pad input device instead of the screen of the display. In absence of a touch device, a device may still accept each type of input action used to zoom, pan, and rotate from another input device such as a mouse, keyboard, and/or the like. These various methods of navigating using a touch-screen device will be discussed in greater detail later in this disclosure.

Returning now to the way records are linked in the chart, the relationship between two records may be more complicated than the adjacent records in the parent-child relationship 115. The relationship between two nodes may span multiple generations and may be comprised of myriad legal and familial bonds. In one embodiment, a genealogical tree structure may represent these more complicated relationships using multiple nodes and interconnecting relationships to form complicated topographies. A complicated relationship may be represented as the sum of a plurality of individual relationships. For example, the relationship between node 110 and node 130*a* may be comprised of the nodes 110 and 120*a* and the relationship 115*a* between them (a parent-child relationship), nodes 120*a* and 130*a* and the relationship 125*a* between them (another parent-child relationship).

Because complex genealogical trees may be comprised of multiple simple relationships, it may often be difficult to display all of the relevant information at the same time on a single display device, particularly a touch-screen device with a small screen. Because a complex relationship may be constructed by multiple individual records and relationships, this relevant information may include biographical, pictorial, audio, video, documentary information, and/or the like for each of the individual nodes in the relationship pathway. Therefore, in accordance with embodiments of the present invention, methods systems are herein discussed that may display an optimal amount of the genealogical tree in such a way that a user can understand its organization and easily navigate the tree on a touch-screen device.

Figure 2A:
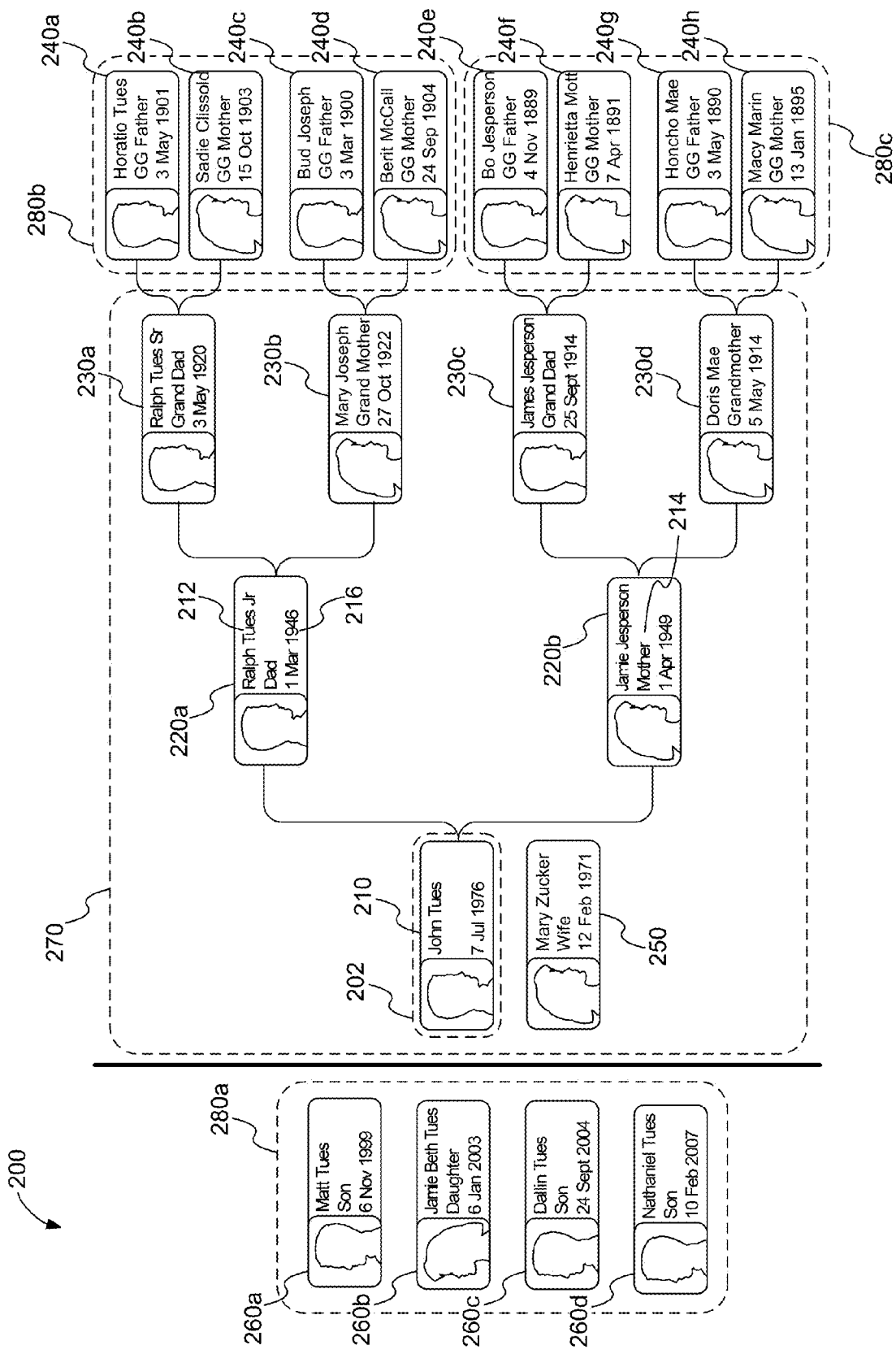
FIG. 2A illustrates a display for a record display program with an exemplary arrangement of icons corresponding to records that are interrelated according to one embodiment.

Given this large amount of information that may be stored in a genealogical tree, it may be impractical to display the entire tree at once. As used herein, the term "display" refers to a graphical representation of various genealogical records. This is separate from the physical device used to make the display visible to a user. For example, in one computer system, the display would refer to the graphical information provided to a processor, to be displayed on a touch-screen device. FIG. 2A illustrates a display 200 for a record display program with an exemplary arrangement of icons corresponding to records that are interrelated. The display 200 provides an easy and convenient way to show the relationships between records (i.e., show how the records are connected). Specifically shown in display 200 is a plurality of icons related to genealogical records. Display 200 may be arranged according to a "relationship view," which simultaneously shows an individual's progeny, ancestry, and siblings. In other words, the display 200 is not restricted to one type of view, such as an ancestral view that only shows a person's ancestors, but the display 200 may show any and all relationships linked to an individual together in various combinations on a display device.

The display 200 may include a plurality of icons or avatars, such as icon 220*a*. Each of the icons may be associated with a specific genealogical record in a database of genealogical records. A computing system may associate each of the records with a specific icon and/or a user can associate each record with an icon. The icon 220*a* may include a figure that visually represents the associated record. For example, the icons displayed in FIG. 2A shows a profile of a woman's head or a man's head to visually represent the sex of the individual associated with the genealogical record. The icons may further be colored to show additional information, such as coloring icons representing females in pink and icons representing males in blue. The icons 210 may further include information about the record that they represent. For example, FIG. 2A illustrates icon 220*a* as including the name 212 and the birth date 216 of the individual.

The display 200 may include a docking field 202 (shown in dashed lines) that focuses the display 200 on a selected record and/or that displays relationship information for the selected genealogical record (e.g., displays a family relationship for the selected record). The docking field 202 may be a predefined area of the display that is configured to receive an icon and display information for the record positioned in the docking field 202. The display 200 may include a visually defined boundary for the docking field 202 or may generally include an area that a user may or may not recognize as being the docking field 202. FIG. 2A illustrates icon 210 that represents a genealogical record for John Tues as being positioned within the docking field 202. Since this icon 210 is positioned within the docking field 202, the display 200 is focused on the record for John Tues and the type of relationship or connectedness of other records linked to the record for John Tues. Thus, the other icons shown in display 200 are arranged according to their relationship or link with the icon 210 representing John Tues. More specifically, the other icons are arranged according to the relationship or link between the records they represent and the record of John Tues.

The display 200 may include one or more progeny or descendant fields 260 that are linked to the docking field 202. The progeny fields 260 may be configured to display the icons of genealogical records that are the progeny or descendants of the person associated with the record/icon 210 positioned in docking field 202. For example, FIG. 2A illustrates the progeny fields 260 disposed to the left side of docking field 202 and including four icons that represent the children of John Tues. The progeny icons in the progeny fields 260 may be arranged according to birth order with the icon for the oldest child vertically above the other icons and the icon for the youngest children vertically below the other icons. The display 200 may also include one or more spouse fields 250 linked to docking field 202 and configured to display the icon associated with the spouse(s) of the person represented by the icon 210 in docking field 202. The spouse field may be positioned vertically below and slightly horizontally offset from icon 210 in docking field 202.

In some embodiments, display 200 may further include a plurality of sibling fields (not shown) that are linked to the docking field 202. The sibling fields may be configured to display the icons of genealogical records that are the siblings of the person associated with the record/icon 210 positioned in docking field 202. The sibling fields may be positioned vertically above and/or below the docking field 202 so that the icons displayed in the sibling fields 208 horizontally align with the icon in the docking field and are vertically offset from one another. The icons in the sibling fields may be arranged according to a birth order so that the icon for the oldest sibling is positioned above the other icons and the icon for the youngest child is positioned below the other icons. Such an arrangement of siblings may visually illustrate where in the birth order the person represented by icon 210 fits within the family.

Display 200 may additionally include a plurality of ancestral fields 220, 230, and 240 that are likewise linked to docking field 202. The ancestral fields 220, 230, and 240 may be configured to display the icons of genealogical records that are the ancestors of the person associated with the record/icon 210 positioned in docking field 202. The ancestral fields 220, 230, and 240 may be positioned to the right of the docking field 202 so that the parent icons in each generation are horizontally offset from the corresponding child icon and vertically offset above and below the centerline of the child's icon as shown in FIG. 2A.

Each of the icons, such as icon 220b, may also include relationship information 214 that describes the relationship between the icon 220b and the icon 210 positioned in the docking field 202, or more specifically the relationship between the records represented by the icons, 210 and 220b. As illustrated in display 200, the icons in the progeny fields 240 indicate whether the individuals are sons or daughters of John Tues, while the icon in the spouse field 250 indicates that the individual is the wife of John Tues, and the ancestral fields 220, 230, and 240 indicate whether the individual is the father, mother, grandfather, grandmother, etc. of John Tues.

Further, although FIG. 2A shows the ancestral fields 220, 230, and 240 running two generations deep and the progeny fields 260 running one generation deep, it should be realized that the fields and/or icons may be arranged in any configuration. For example, the ancestral field 220 may run one generation deep while the progeny fields 260 run three generations deep, or the ancestral fields 220 and 230 and progeny fields 260 may both run two or three generations deep. Further, the docking field 202 may be repositionable on the display 200 so that a user may reconfigure the display 200 according to need and/or preference. For example, a user may enlarge the area defined for docking field 202 and or reposition it vertically and/or horizontally on the display 200.

From FIG. 2A, it should be clear that ancestral and progeny records may be organized into a generational hierarchy with sequential levels. For example, the parent fields 220 may represent a first level of the generational hierarchy, and the grandparent fields 230 may represent a second level of the generational hierarchy. Because most genealogical tress may extend many generations, the display 200 may include a subset of the levels of the generational hierarchy simultaneously. Therefore a determination must be made as to how many generations levels may be displayed at one time on the display 200 such that enough personal information for each record is displayed while maintaining the context within the larger genealogical tree. Therefore, a display group 270 may be formed to include the graphical information for each record displayed in the touch-screen.

In one embodiment, a predefined number of generational levels may be displayed. For example, a display group 270 having a predefined target number of three generational levels may be formed, comprising the selected record in the docking field 202, the parent ancestral fields 220 and the grandparent ancestral fields 230. The target value may be defined in hardware or software and/or changed by the user. It may also be calculated based on a hardware profile or characteristic, such as available memory, the size of the display, and/or the like.

In another embodiment, instead of being a hard target, the predefined number may instead be a minimum value, a maximum value, or an approximate target. When the predefined target value is approximate or a minimum/maximum, the actual number of generational levels in the display group 270 may be influenced by other factors such as icon display size, total number of records in the relationship, and/or the like. Merely by way of example, a user could decrease the amount of information to be displayed for a record, and this in turn could increase the number of generational levels displayed in each set up to a maximum target number of generational levels. Alternatively, the user could increase the amount of information displayed in each node, and the number of nodes displayed could decrease down to a minimum target number of generational levels.

In another embodiment, the number of generational levels in the display group 270 may depend on a minimum, maximum, or target relationship span. For example, FIG. 2A shows the display group 270 comprised of a number of generational levels wherein the relationship span between the first and last records in the display 200 is a grandparent-grandchild relationship. The relationship span may be a hard number, or it may be an approximate target that is used in conjunction with other display variables to calculate the actual number of nodes in the display group 270.

While the ancestral and progeny records may be organized into a generational hierarchy with sequential levels, they may also be organized into familial lines. For example, at least three familial lines may extend from the John Tues's icon in the docking field 202. The paternal familial line would run through John Tues's father (Ralph Tues Jr.) in icon 220a. The maternal familial line would run through John Tues's mother (Jamie Jesperson) in icon 220b. Finally, a third family line would run through John Tues himself towards his children represented by his children's icons 260. When navigating around the display 200, a user may typically navigate along these or other similar familial lines.

In yet another embodiment, the number of generational levels in the display group 270 may change dynamically as the display parameters are changed. For example, the display group 270 containing three generational levels may be reorganized to contain more than three generational levels if a user provides a command to zoom out the display 200. As another example, a user may set the display 200 to show a particular subset of the genealogical records simultaneously on the display screen. The number of generational levels in the display group 270, the span of the relationships in the display 200, or some other variable based on the user selection may be used as a basis for organizing or reorganizing the display group 270. The same process for dynamically sizing the steps in the sequence described above could be used in response to any change in the display, such as panning, zooming, changes in resolution, changes in display size, and/or the like. It should be appreciated in light of this disclosure that these methods of determining a number of generational levels to include in the display group 270 are merely illustrative, and that other combinations and variations of these techniques for doing such may be used in other embodiments.

As stated above, various finger gestures may be used to manipulate the display 200 and navigate around a genealogical chart. Specifically, a finger gesture may be used to replace icon 210 in the docking field 202 with another icon, and rearrange the genealogical records in the display group 270 accordingly. Finger gestures may be used to graphically move the display group 270 in FIG. 2A a number of generational levels to the left or right. In order to provide for a seamless, animated graphical transition between two successive display groups, the records in the next generational levels that are not in the current display group 270 may be prepared for display prior to receiving a user input requesting such. The display information for these groups may be prepared and stored, or "pre-fetched", in a cache memory such that the as the records in the display group 270 are shifted in and out along familial lines, high latency memory operations may be eliminated.

For example, if the display 200 is configured to advance one generational level in either the ancestral or progeny directions in response to a navigation and/or pan command, then the cached display groups 280 may be prepared for display and stored in a cache memory. If the display 200 is navigated in the paternal ancestral direction, then the cached display group 280b could be incorporated into the display group 270 without requiring additional high-latency memory and/or display operations.

Figure 2B:
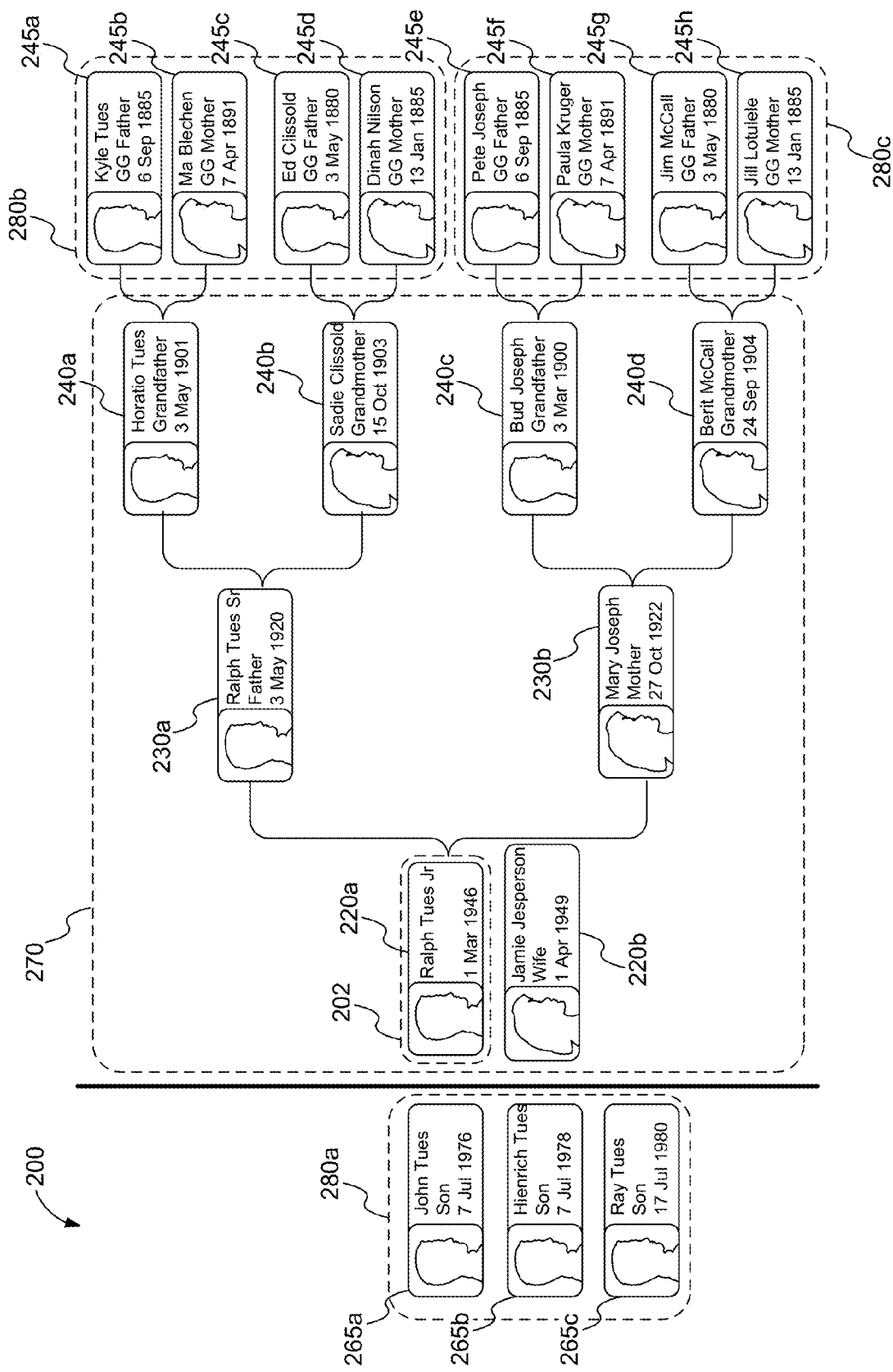
FIG. 2B illustrates a transition between different display groups according to one embodiment.

FIG. 2B illustrates a transition between different display groups according to one embodiment. For example, if the display 200 received a finger gesture associated with navigating the display along the paternal ancestral line, then the display groups and the docking field could change accordingly. Specifically, icon 220a associated with the record for Ralph Tues Jr. has been transferred from the ancestral field (specifically the father field) into docking field 202. As icon 220a transfers into docking field 202, the other icons in display 200 may transfer into one or more fields based on the relationship between the records of these icons and the record of icon 220a, which is now the focus of display 200. For example, icons 240a and 240b, which represent the respective father and mother records of Ralph Tues Jr. (icon 220a) may transfer from grandfather and grandmother fields to father and mother fields based on a father and mother relationship with the record represented by icon 220a. All moving icons may appear to move simultaneously with or near simultaneously with icon 220a so that the context of the relationship is maintained.

One way to keep the relationship context intact is to transition or transfer all the icons simultaneously or nearly simultaneously so that it appears to a user that all the icons transfer/shift at once while maintaining a linked arrangement. Maintaining a linked arrangement may include maintaining spatial dimensions between icons so that it appears as if the icons are physically linked together. Another way to keep the relationship context intact is to transfer, transition, or otherwise shift and move icons without refreshing or redrawing display 200, which helps keep the focus and attention on the icons and relationships between icons/records. The transfer or replacement of an icon in docking field 202 changes the focus of the information and relationships in display 200 from the record for the transferred or replaced icon to the record for the new icon. For example, the sibling, ancestral, and/or progeny links may change to reflect the shift in focus to the new icon positioned in docking field 202. If these fields were not previously in the display group 270, they could be thereafter be included.

Similarly, any siblings fields and docking fields may transition to the progeny fields due to these icons representing the children of the Ralph Tues Jr. (represented by icon 220a). Likewise, icon 210 representing John Tues may transition out of the docking field 202 so that the focus of display 200 is shifted from the record of John Tues to the record of Ralph Tues Jr., or any other record that is positioned within docking field 202. As previously described any sibling icons may transfer or transition simultaneously with or nearly simultaneously with icon 220a so that the transition is visually seamless or substantially visually seamless to a user and the context of the relationship is maintained.

As the focus of display 200 shifts from the record of icon 210 to the record of icon 220a, one or more records may be transitioned or transferred off display 200. For example, the progeny icons 270 may be transferred from the progeny fields so that the icons are no longer visible on display 200. This may be due to the user configuring display 200 to only display one generation of descendants. Similarly, icons 230c and 230d, which represent the father-in-law and mother-in-law of the record of icon 220a may be transferred from the ancestral fields so that these records are no longer displayed because there may be no ancestral relationship between these records and the record of icon 220a.

Similarly, icons representing records that were not originally displayed in FIG. 2A may be transferred or transitioned into the display 200. For example, the grandparent records 245 linked to the record of icon 220a may be transferred onto display 200 so that the previously un-displayed grandparent icons of Ralph Tues Jr. may be subsequently displayed. FIG. 2B illustrates the previously un-displayed icons repositioned in the grandparent fields replacing icons 240. Likewise, previously un-displayed sibling icons of Ralph Tues Jr. (not shown) may be displayed as well, and may be transferred onto display 200 and subsequently populate the respective sibling fields based on their relationship to the record of icon 220a. Further, the replaced icons may transfer to new fields and/or on or off display 200 simultaneously or nearly simultaneously to provide a visually seamless transition and thereby keep the relationships between the records in context during the transition. Additionally, display 200 may curve hyperbolically toward the edges of the display so that icons transferred on and/or off display 200 curve behind one another toward the edge of the display thereby enabling several generations of icons to be visible toward the display's 200 edge.

Transferring icons to and from the docking port 202 may occur in a variety of ways, such as through scrolling, selecting and dragging an icon, moving an imaging device, etc. For example, a user may use a scroll button to scroll between records displayed in docking field 302 or may place a finger and/or mouse pointer on a display device (e.g., a selectable LCD screen) and scroll through records displayed in docking field 202 by dragging the finger and/or mouse pointer across the display device. The user may move a finger and/or mouse pointer vertically as well as horizontally to navigate between records, such as by dragging a finger diagonally up and right to transfer icon 220a to docking field 202. In this manner, a user may quickly and conveniently scroll through numerous records and across multiple generations (forward and backward) by merely positioning a mouse pointer. If the record database is large, the user may further quickly and conveniently scroll horizontally through multiple generations and scroll vertically through multiple family lines so that the displayed record at the end of the scrolling session is tenuously related to the record displayed at the beginning of the scrolling session.

In addition to scrolling, the user can position icons in the docking field 202 by selecting an icon from one of the fields and dragging the icon to the docking field 202. For example, icon 230a representing Ralph Tues Sr. may be selected and dragged from the father field to the docking field 202 so that the focus of the display 200 is transferred to the record of icon 230a. The transfer or transition of the icons between fields and/or on or off the display 200 may occur simultaneously or near simultaneously as described above.

Similarly, the display device may be configured to recognize a position change of the display device to allow a user to navigate between records by physically moving the display device. For example, if the display 200 is displayed on a hand-held device, a user may move the hand-held device vertically and/or horizontally to navigate between the icons positioned in the docking field 202. The icons may appear fixed in space and/or the icons move on or off the display as the wireless device is moved. Such a configuration is similar to moving a transparent piece of glass and viewing icons behind the glass, where the icons remain fixed in space, but they enter or exit the glass display as the glass is moved in relation to the icons.

Further, although FIG. 2B has been described as transferring or transitioning an icon from an ancestral field into the docking field 202, it should be realized that an icon can be transferred into the docking field 202 from any field of display 200 and/or from an area off the display 200. For example, an icon in a sibling field or progeny field may be transferred to the docking field 202 to focus the display 200 on the sibling record or descendant/progeny record. Thus, display 200 is capable of moving in any direction (horizontal, vertical, diagonal) through a genealogical record. Similarly, the docking field may be selected, which may open a browse window so that a user can select a record and icon to display in docking field 202.

In addition to relocating the various icons on the display 200 when the icon in the docking field 202 is changed, the various display groups 270 and 280 may also be repopulated. For example, in FIG. 2B, the transition from icon 210 to 220a in the docking port 202 may render the original cached display groups 270 and 280 partially obsolete. Ancestral cached display groups 280b and 280c may be repopulated with the great-grandparents of Ralph Tues Jr., which are represented by the great-grandparent icons 285. Similarly, the progeny cached display group 280a may be repopulated with the previously docked icon 210 of John Tues, along with John Tues's siblings icons 265.

The transition illustrated between FIG. 2A and FIG. 2B is merely illustrative, and in light of this disclosure, it will be understood that many variations on these transitions may be possible in other embodiments. For example, these figures show a transition between two consecutive generations; however, other embodiments may include transitions between multiple generational levels, and may consequently require that the cached display groups 280 include more than a generational level. Each movement up the paternal ancestral line in FIG. 2A may move two generational levels. Thus, a single finger gesture, such as a swipe motion, may transfer a member of the grandparent generational level to the docking port 202. In order to be prepared for a two-generation transition, the cached display groups 280 could contain two generational levels so that they could be pulled into the display group 270 at the transition without requiring high-latency memory operations.

Furthermore, the number of generational levels in the cached display groups 280 need not equal the number of generational levels that are moved during a transition. For example, if each transition spanned two generational levels, the cached display groups 280 could include three or four generational levels. In this case, the needed generational levels could be transitioned out of the cached display groups 280 and the next generational levels could be transitioned in, such that at least one generational level could persist in the group both before and after a transition. Such a configuration could be advantageous to accommodate rapid transition commands, such as multiple successive finger swipe gestures.

Figure 2C:
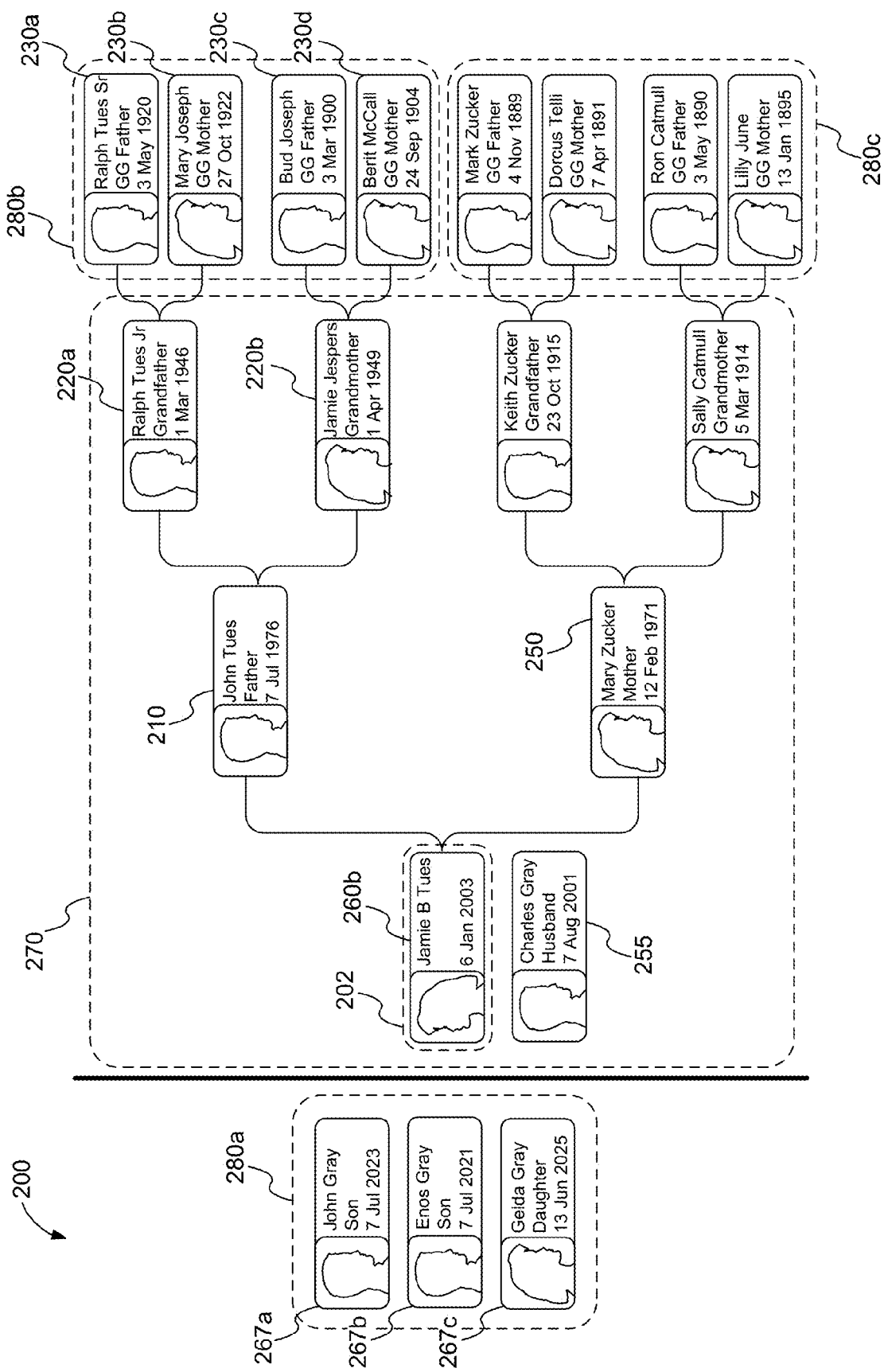
FIG. 2C illustrates another transition between different display groups according to one embodiment.

As stated earlier, navigation between records in the display 200 may take place in any direction. FIG. 2C illustrates a transition between genealogical records in the progeny direction of the genealogical chart. This processes is very similar to the transitions made down the ancestral line illustrated in FIG. 2B. Here, John Tues's icon 210 is replaced in the docking port 202 with his daughter's icon 260b representing Jamie Tues. In turn, Jamie Tues's spouse, Charles Gray, has his icon 255 placed in the spouse field below Jaime Tues's icon 260b. The icons 267 for the children of Jamie and Charles may be imported into the child fields, and the ancestral line of the Mary Zucker (icon 25) may be included in the display 200. As before, this transition may occur as a continuous, seamless animation such that the relationships between each of the records may be visually maintained.

Figure 3A:
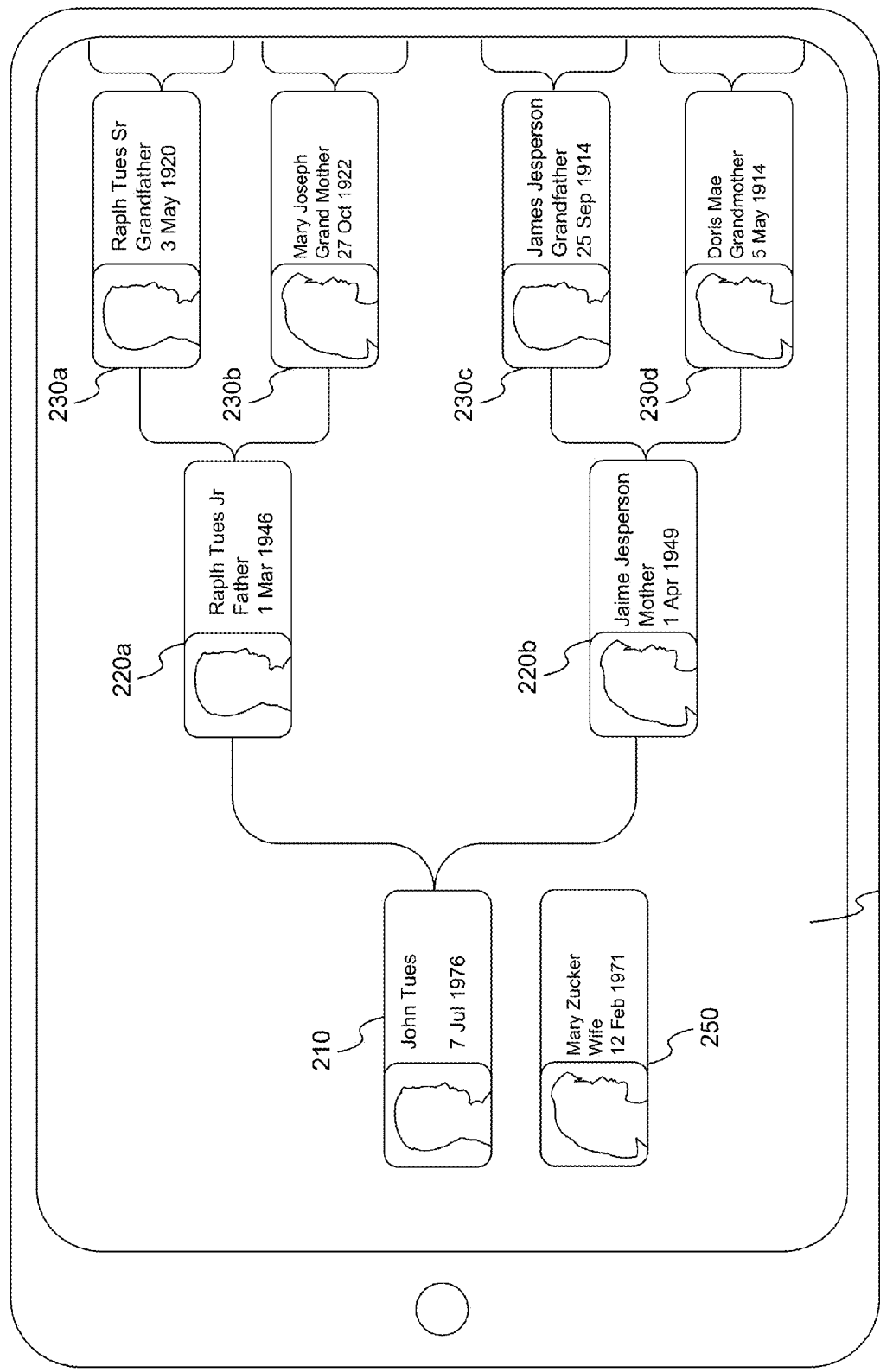
FIG. 3A illustrates the display of a portion of a genealogical chart on a touch-screen device according to one embodiment.

As stated earlier, there exists many ways to effect a transition between records. Given the increasing prevalence and quality of mobile touch-screen devices, the portable touch-screen interface may become of increasing importance to genealogical research. Consequently, in the future the use of finger gestures in conjunction with a touch screen may become an increasingly important means for transitioning between various genealogical records. FIG. 3A depicts the display of a portion of a genealogical chart on a touch-screen device 301. The genealogical records displayed on the touch-screen 300 correspond to the display group 270 from FIG. 2A. Accordingly, the icon 210 of John Tues occupies the docking port 202. Note that in the display, the docking port 202 is not visible to a user. In this embodiment, the docking port 202 is simply an area on the screen wherein the genealogical record of focus will generally reside, in this case icon 210. Although this embodiment depicts a touch-screen device 301 that resembles an iPhone® or iPad®, any touch-screen device may be used with various embodiments.

In order to navigate around the genealogical chart and reveal genealogical records that are not currently depicted on the touch-screen display 300, the touch-screen 300 may accept finger gestures received via the touch-screen 300 as user commands. Specifically, finger gestures may be accepted that contain directional information. The directional information from the gesture may be correlated with the directions of the various ancestral, sibling, and/or progeny lines of the genealogical records being displayed. Depending on the location, direction, and velocity of the finger gesture on the touch-screen display 300, it may be determined that the gesture corresponds to a command to transition the genealogical records in a corresponding direction.

Figure 3B:
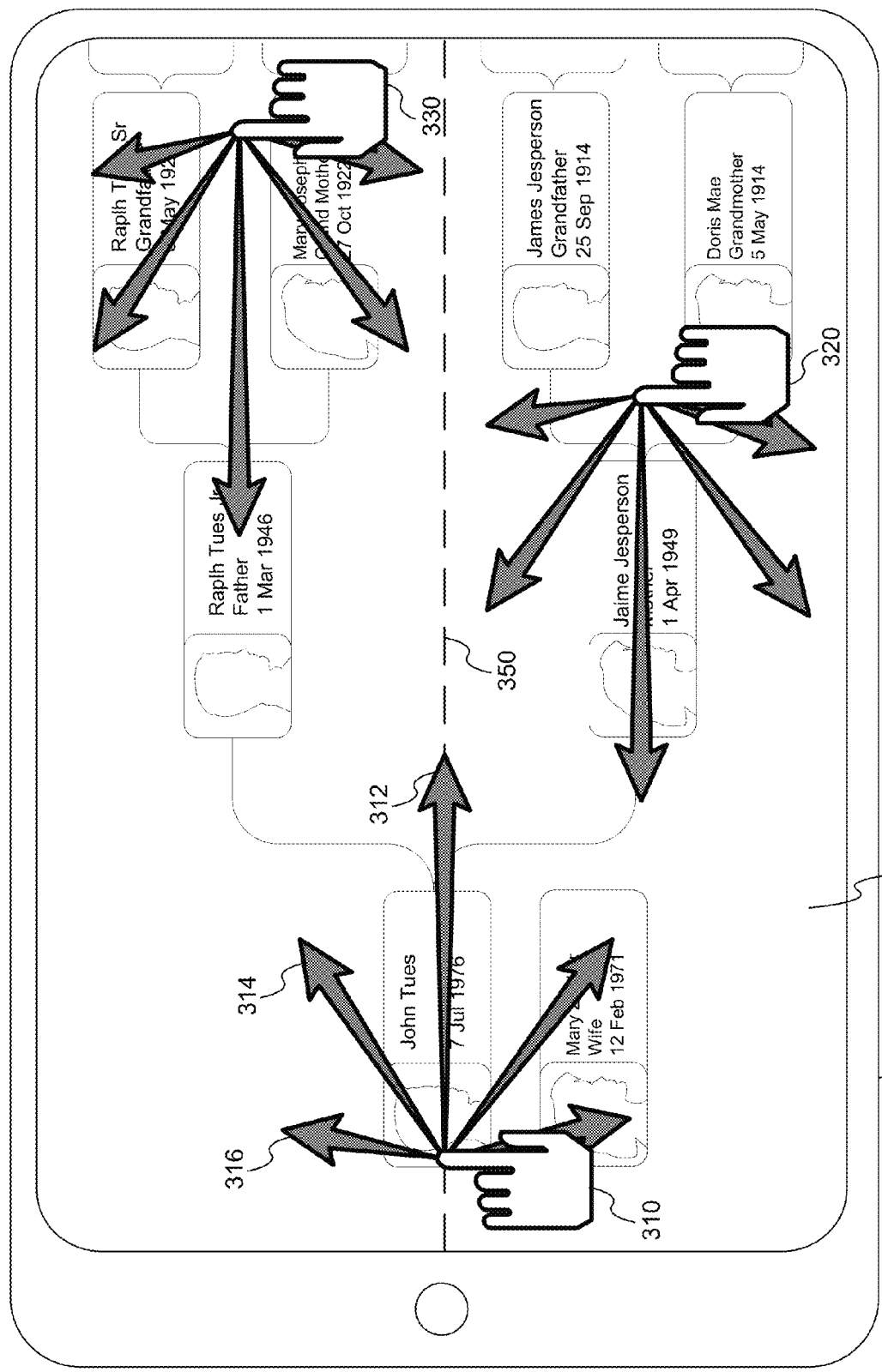
FIG. 3B illustrates various examples of finger gestures that may be accepted from the touch-screen according to one embodiment.

FIG. 3B illustrates various examples of finger gestures that could be accepted from the touch-screen 300. Specifically, the display group 270 is depicted on the screen with three types of finger gestures. Generally, there are a number of different types of finger gestures that may be used to pan a display. The most common are the scroll (or drag) and the swipe (or fling). The scroll/drag gesture occurs when a user places a finger in a first location on the touch-screen 300 and drags it to a second location while maintaining contact with the touch-screen 300 before, during, and after the drag. The measurements that are of consequence during a scroll/drag are the starting and ending locations. From these, the display may be moved a proportional distance on the touch-screen 300. In contrast, a swipe/fling gesture corresponds to a user dragging a finger across the touch-screen 300 at or above a certain velocity and then lifting the finger from the touch-screen 300 at the end of the gesture. The measurements of interest in a swipe/fling are the starting and ending locations and the velocity of the gesture. From these, the display can be "flung" on the touch-screen farther than the proportional distance between the starting and ending points of the gesture. Various embodiments may use these two types of finger gestures interchangeably to pan the display of the genealogical charts.

It is important to note that various embodiments of this invention may use many different types of finger gestures. Some embodiments may also use various different methods of deriving a directional component from a finger gesture and correlating the derived direction with a direction of a familial line in the genealogical chart. The appended figures show only a few examples of the possible gestures and how they may be analyzed to navigate around a genealogical chart. It will be understood in light of this disclosure that these examples are not limiting, but are instead one way of implementing this invention. Therefore, the details provided below are described only to provide an enabling disclosure, and are thus only illustrative. For example, many different graphical arrangements of genealogical records on the touch screen 300 are possible, which could result in many different directional possibilities. Also, many different types of gestures and inputs could be accepted and mapped as directional navigation commands. Consequently, the left and right swipes described below could be replaced by other directions and gestures, and the graphical layout of the genealogical charts could be replaced with other layouts with multiple directional possibilities.

In one example, shown in FIG. 3B there are at least three directions that the display may be panned. The first direction is towards additional progeny information towards the left side of the touch-screen 300 using a right swipe 310. Any swipe with a vector angle of between about 0° and 90°, and between 270° and 360° would qualify as a right swipe 310. In other words, any swipe with a horizontal component towards the right side of the touch-screen 300 could be considered the right swipe 310. Also, a fling, scroll, or drag gesture as described above, or any other directional finger gesture with a rightward component, could be considered the right swipe 310.

The magnitude of the vectors 312, 314, and 316 emanating from the right swipe 310 have been drawn to be graphically proportional to the resulting magnitude of the rightward horizontal component of a swipe in that direction. For example, vector 312 is the longest because substantially all of the magnitude of a rightward swipe will translate into the horizontal component. Therefore, a swipe that is substantially in the rightward direction will result in a motion on the touch-screen that is proportional to the overall swipe magnitude. In contrast, a swipe in the direction of vector 316 would have a relatively small horizontal component, and the resulting rightward magnitude would be small compared to that of vector 312. Again, this is merely an illustrative example illustrating only navigation in a purely horizontal direction to the left. Other configurations may incorporate both the horizontal and vertical components of the swipe motion.

When a right swipe 310 with sufficient velocity and/or distance has been detected, the display 200 that is displayed on the touch-screen 300 may add and/or remove genealogical records according to the direction of the swipe. For the right swipe 310, the display may add the cached display group 280a, comprised of the children of John Tues (icons 260a-260d). Additionally, icons 230a-230d displaying the grandparents of John Tues could be removed from the display. Following the right swipe 310, the display group 270 could resemble the display group 270 in FIG. 2B. In some embodiments, the transition could be a seamless animation that visually preserves the connecting relationship information. Also, the grandparent records in icons 230a-230d could be shifted into a cached display group, and the next generational level in the progeny of John Tues could be shifted into the cached display group 280a.

The left swipes 320 and 330 in FIG. 3B illustrate a more complex example of extracting directional swipe information for multiple ancestral lines extending off the touch-screen 300. In the embodiment shown, there are two familial lines that extend off of the right side of the touch screen 300: the paternal family line, and the maternal family line. Because these extend off of the right side of the screen rather than the top or bottom, the leftward horizontal motion vectors from a finger gesture may be extracted in the same manner as they were in the case of the right swipe 310. In order to determine whether the paternal or maternal family lines are followed, the starting point of the swipe may be determinative. For example, the touch-screen may be divided into two vertical sections by line 350. If the left swipe 330 begins above line 350, then the paternal line through Ralph Tues Jr. in icon 230a may be followed, cached display group 280b comprising icons 240a-240d may be imported into the display group 270, and John Tues and his siblings in icons 265a-265c may be shifted into cached display group 280a. On the other hand, if the left swipe 320 begins below line 350, then the maternal line through Jamie Jesperson in icon 230b may be followed, cached display group 280c comprising icons 240e-240h may be imported into the display group 270, and John Tues and his siblings in icons 265a-265c may be shifted into cached display group 280a.

Using the line 350 in the center of the screen to distinguish between a finger gesture intended to follow either the paternal or maternal line is only one method of extracting directional information from a gesture and correlating it with a familial line. In other embodiments, the horizontal and vertical components may be used to determine a direction. For example, a substantially diagonal gesture aimed towards the top right side of the screen could follow the paternal line, while a substantially horizontal gesture towards the right side of the touch screen 300 could follow both the maternal and paternal lines and incorporate all of the grandparent icons 230 into the display 200. It will be understood in light of this disclosure that a gesture may be accepted in any direction, and that the genealogical chart may extend off of the touch screen 300 in any direction. This may include diagonal and vertical orientations that represent complex familial and legal relationships between genealogical records. It will also be understood that the terms "left", "right", "top", "bottom", "above", and "below" are all relative and used to describe the touch screen 300 orientation in FIG. 3B. As the touch-screen device 301 is rotated or the layout of the display 270 is changed, the relative motions and directions may change as well.

Figure 4A:
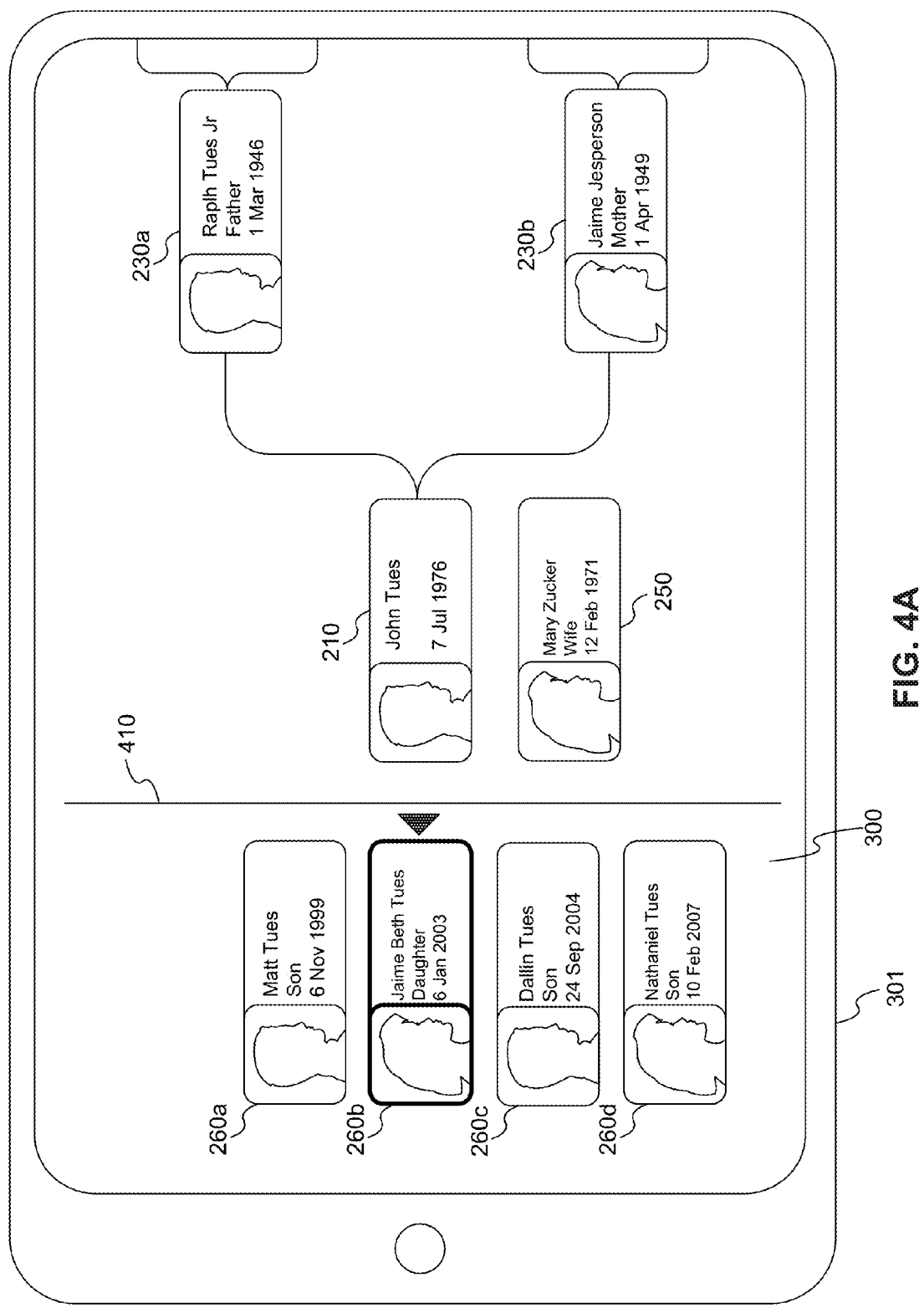
FIG. 4A illustrates the display of another portion of a genealogical chart on a touch-screen device according to one embodiment.

FIG. 4A illustrates one of many alternative configurations for the display 200 on the touch-screen 300. In this embodiment, the display 200 on the touch-screen 300 is divided by a vertical separator 410. Both progeny line icons 260 and ancestral icons 230 are displayed together. Progeny icon 260*b* designated as the progeny line to follow if the touch-screen accepts a directional finger gesture correlated with leftward navigation through the genealogical chart. The designated progeny icon 260*b* may be highlighted by color, border, graphic, and/or the like. However, in this configuration, finger gestures can also be used to move the progeny icons 260 up and down in order to select amongst the different children's lines. Various other commands and gestures can be used in combination with directional navigation commands to increase the responsiveness and functionality of the interface.

Figure 4B:
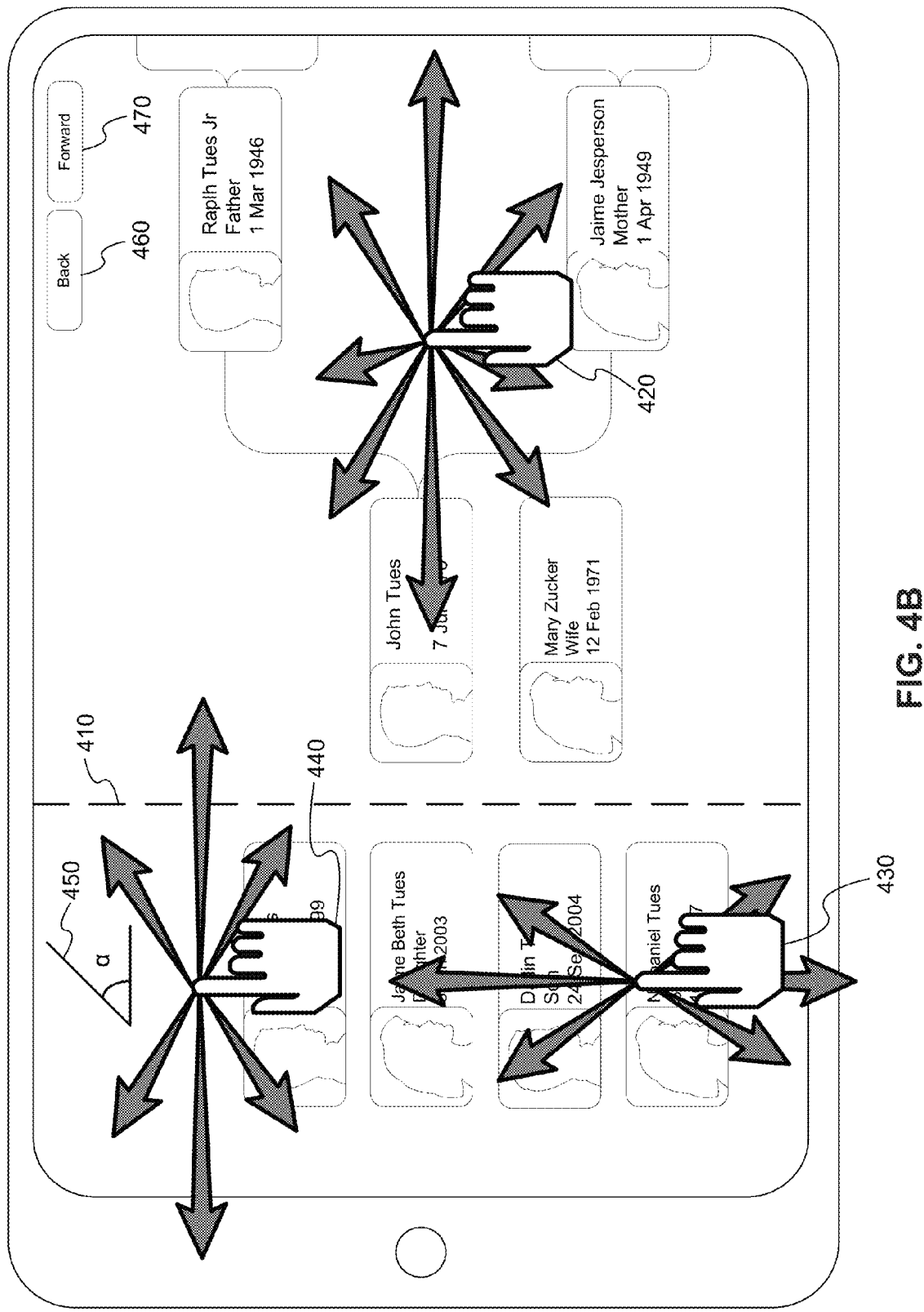
FIG. 4B illustrates various additional examples of finger gestures that may be accepted from the touch-screen according to one embodiment.

FIG. 4B illustrates a subset of the possible finger gestures that may be used to manipulate and navigate the genealogical chart that from FIG. 4A. In this embodiment, directional swipe 420 may be used to navigate the display to both the left and the right. As before, the horizontal component of the directional swipe 420 may be extracted and used to determine the direction of the navigation. Although not shown in this embodiment, a vertical component could also be used if there were familial lines that extended vertically off of the touch-screen 300.

Of importance here is the starting point of the swipe gesture. If the starting point of the swipe is to the right of the dividing line 410 (like directional swipe 420) then the any swipe that is substantially non-vertical may have the horizontal components mapped to a horizontal navigation through the genealogical chart. However, if the starting point of directional swipe, such as swipes 430 and 440, is located on the left side of the vertical separator 410, then the vertical components may also be considered. In the embodiment shown in FIG. 4B, a critical angle 450 may be used to determine whether a swipe gesture beginning to the left of the vertical separator 410 should be considered a horizontal navigation command, or a vertical command to scroll up and down through the progeny icons 260. For example, directional swipe 440 includes only swipes that are less than the critical angle 450 (about 45°) and therefore the horizontal components of the directional swipe 440 could be used as a horizontal navigation command. On the other hand, directional swipe 430 includes swipes that begin to the left of the vertical separator 410 that are greater than the critical angle 450. Here, the vertical component of the directional swipe 430 may be used as a scrolling command to move the progeny icons 260 up and down.

Additionally, the touch screen 300 may include various navigational buttons. These might include a back button 460 and a forward button 470. If a back button 460 command were accepted, then the display could revert back to a previous version. After one or more back button 460 commands, a forward button 470 command could revert back to the previous version of the display prior to the last back button 460 command.

The embodiments in FIG. 3 and FIG. 4 are merely illustrative. Other embodiments may combine elements of these configurations to capture diagonal and vertical navigation in all directions. They could also include many different graphical representations and arrangements of genealogical charts.

Figure 5:
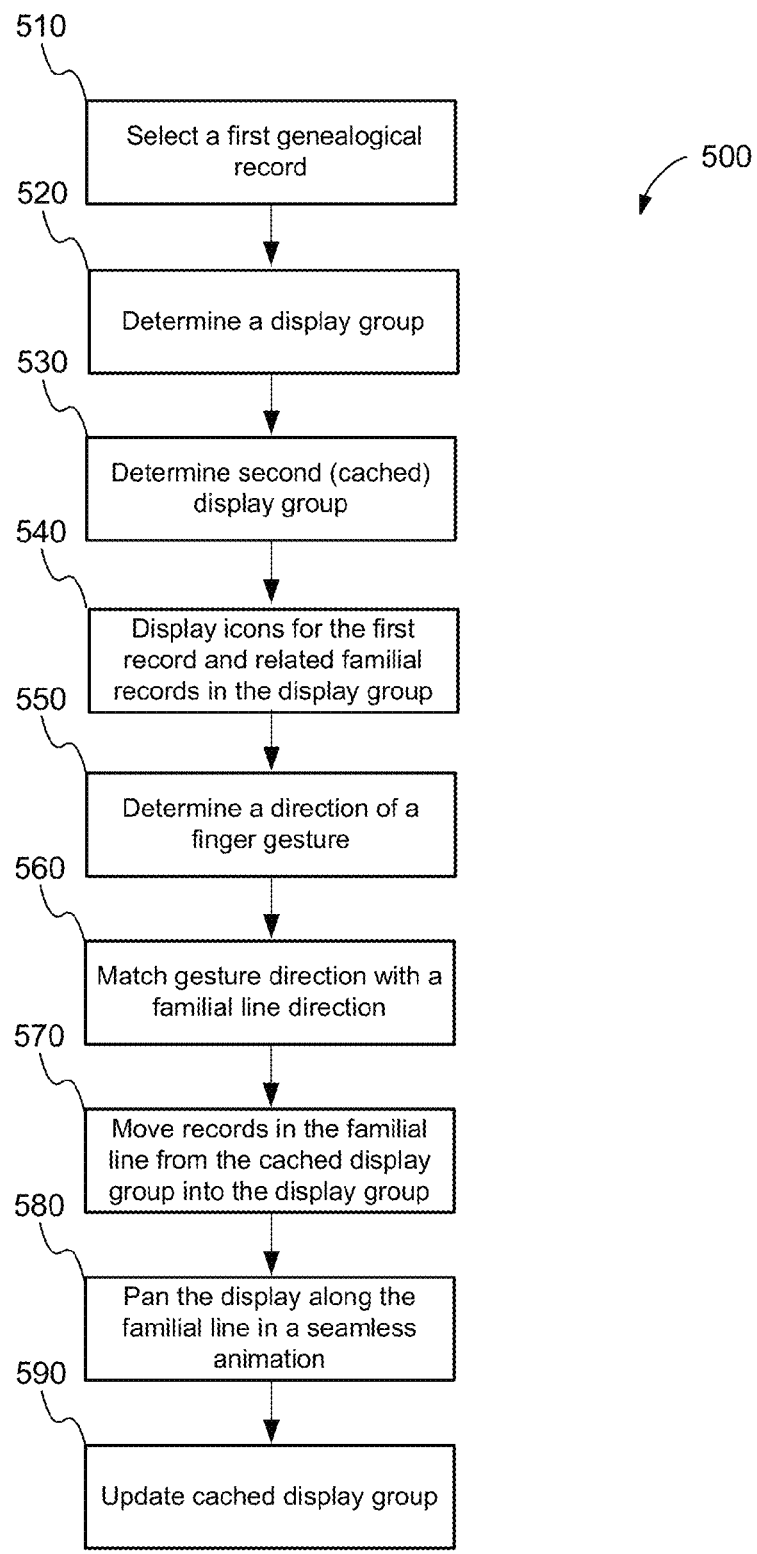
FIG. 5 illustrates a flowchart for using touch-screen finger gestures to navigate through a genealogical chart according to one embodiment.

FIG. 5 illustrates a flowchart 500 for using touch-screen finger gestures to navigate through a genealogical chart. At process block 510, a first genealogical record may be selected from a plurality of genealogical records stored in a memory of a computer system. The first genealogical record may be selected by any input means on a touch-screen device, the means including a finger gesture, a finger tap, a keyboard input, a voice input, and/or another software process. Based on the selected first record, a set of familial records that are related to the first record along familial lines may be selected from the plurality of genealogical records. In some embodiments, this would preclude parallel relationships such as cousins, aunts, and uncles, while other embodiments may include such records.

From these familial records, process block 520 may create a display group made up of at least the selected record and the most immediate familial records along one or more of the familial lines extending from the selected record. In one embodiment, the display group may comprise maternal and paternal family lines extending two generations to include the selected record's grandparents. Another embodiment also includes a progeny line including the selected record's children. The size of the display group may be determined statically based on a user input or saved target number, or it may be sized dynamically according to the techniques described elsewhere in this disclosure. In process block 530, a second display group may be determined to include at least the next familial record in each of the familial lines in the first display group. This second display group may be created so that the display information for these records, i.e., the display icons and connecting relationships, may be prepared and possibly stored in a low-latency cache memory.

In process block 540, the icons for the first display group may be displayed on the touch screen device. In one embodiment, the selected first record may occupy a docking field in the display that focuses the display on the selected first record and causes the rest of the icons in the display group to be positioned relative to the docking field according to familial relationships.

In process block 550, a finger gesture on the touch screen device may be received, and a direction of the finger gesture may be determined. The direction may be based on the direction of the gesture, the directional vector components of the gesture, the velocity of the gesture, the stating and/or ending points of the gesture, and/or the like. In process block 560, the direction of the gesture may be matched with a direction associated with one of the familial lines in the first display group. For example, in one embodiment, a finger gesture direction oriented to the upper right-hand corner of the touch screen may be matched, associated, or correlated with the direction of the paternal line of the first selected record. After the direction is matched, the records in the second, or cached, display group may be associated with the display group in process block 570. This need not involve the actual movement of data between various memory locations, but rather it may include only conceptually including certain records from the second display group in the display group. For example, all the records in the display group and the second display group may be stored in the same contiguous cache memory block. On the other hand, the two display groups may occupy separate blocks in separated memories, such as a processor cache or register bank, and a Level I memory cache.

In process block 580, the actual display may be panned along the familial line designated by the direction of the finger gesture. The pan of the display may be as a continuous animation that appears seamless to a user without a noticeable refreshing or reloading of the touch-screen contents. The pan of the display may also cause any visible relationship indicators to persist throughout the animation such that a user may be able to continuously view the relationship during the transition. For example, a line connecting the selected record's father to its grandfather may alter its route while maintaining the connection after a finger gesture in the direction of the paternal familial line. Thus, the connection line would always connect the father and grandfather as the father's icon was repositioned in the docking field and the great-grandparent's icons were shifted into the display. Finally, in process block 590, the display groups may be updated such that records in certain family lines may move from the display group to the second display group, and certain records that were not stored in either the display group or the second display group may be included therein. This may allow a touch-screen device to rapidly accept finger gestures to pan the display back and forth along various familial lines without a visibly noticeable delay in displaying records that were previously off the screen.

Figure 6:
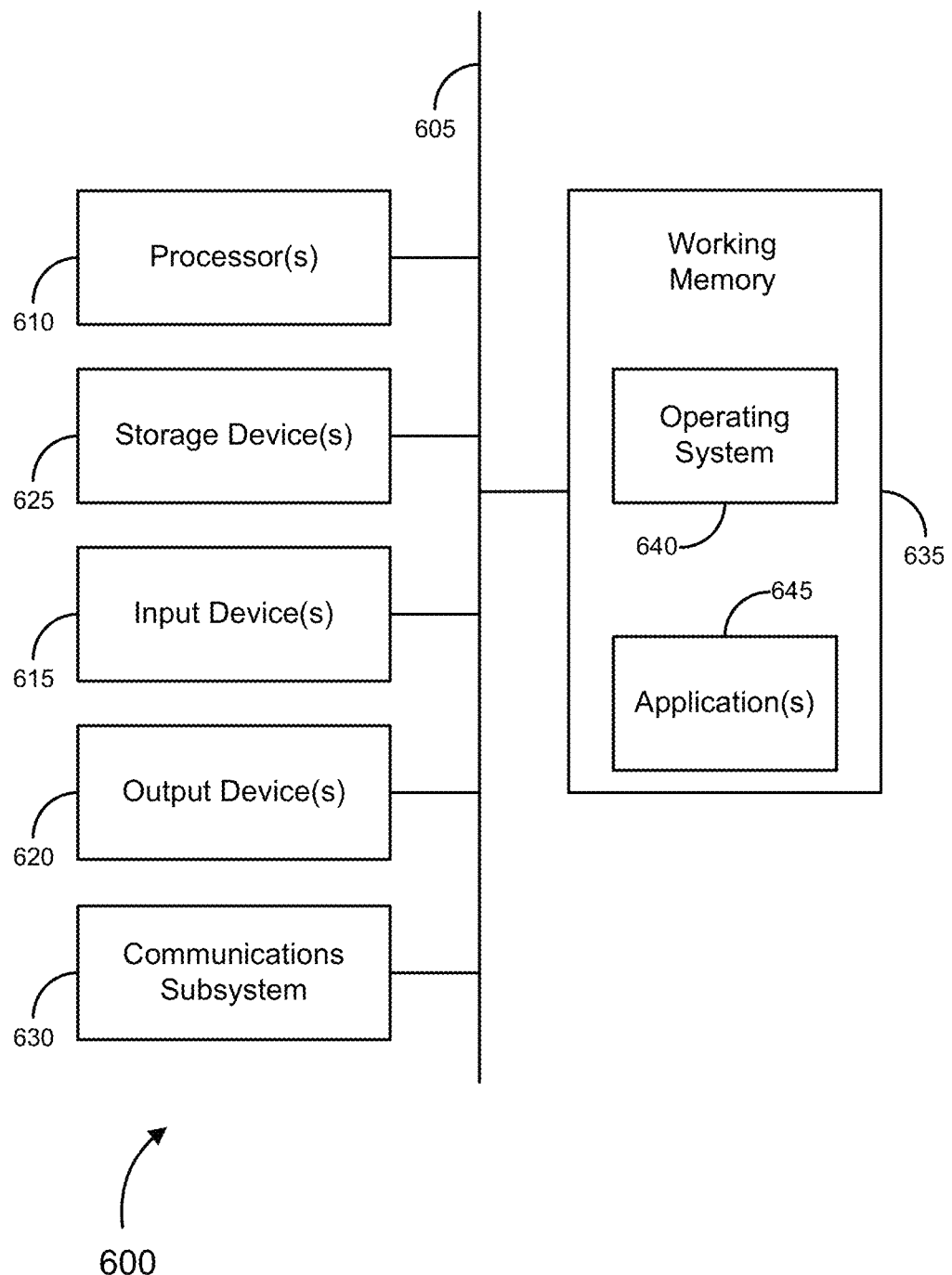
FIG. 6 is a generalized schematic diagram illustrating a computer system for implementing aspects of the present invention.

FIG. 6 provides a schematic illustration of one embodiment of a computer system 600 that can perform the methods of the invention, as described herein. It should be noted that FIG. 6 is meant only to provide a generalized illustration of various components, any or all of which may be utilized as appropriate. FIG. 6, therefore, broadly illustrates how individual system elements may be implemented in a relatively separated or relatively more integrated manner.

The computer system 600 is shown comprising hardware elements that can be electrically coupled via a bus 605 (or may otherwise be in communication, as appropriate). The hardware elements can include one or more processors 610, including without limitation, one or more general purpose processors and/or one or more special purpose processors (such as digital signal processing chips, math co-processors, floating-point units, graphics acceleration chips, and/or the like); one or more input devices 615, which may include without limitation a mouse, a keyboard and/or the like; and one or more output devices 620, which can include without limitation a display device, a printer, multi-touch (e.g., Apple™ iPhone, Apple™ iPad, Microsoft™ Surface™, etc.) and/or the like.

The computer system 600 may further include (and/or be in communication with) one or more storage devices 625, which can comprise, without limitation, local and/or network accessible storage and/or can include, without limitation, a disk drive, a drive array, an optical storage device, a solid state storage device such as a random access memory ("RAM") and/or a read-only memory ("ROM"), which can be programmable, flash updateable and/or the like. The computer system 600 might also include a communications subsystem 630, which can include without limitation a modem, a network card (wireless or wired), an infrared communication device, a wireless communication device and/or chipset (such as a Bluetooth™ device, an 902.11 device, a WiFi device, a WiMax device, cellular communication facilities, etc.), and/or the like. The communications subsystem 630 may permit data to be exchanged with a network (such as the network described below, to name one example), and/or any other devices described herein. In many embodiments, the computer system 600 will further comprise a working memory 635, which can include a RAM or ROM device (as described above), a cache memory, registers, and/or the like.

The computer system 600 also can comprise software elements, shown as being currently located within the working memory 635, including an operating system 640 and/or other code, such as one or more application programs 645, which may comprise computer programs of the invention, and/or may be designed to implement methods of the invention and/or configure systems of the invention, as described herein. Merely by way of example, one or more procedures described with respect to the method(s) discussed above might be implemented as code and/or instructions executable by a computer (and/or a processor within a computer). A set of these instructions and/or codes might be stored on a computer-readable storage medium, such as the storage device(s) 625 described above. In some cases, the storage medium might be incorporated within a computer system, such as the system 600. In other embodiments, the storage medium might be separate from a computer system (i.e., a removable medium, such as a compact disc, etc.), and is provided in an installation package, such that the storage medium can be used to program a general purpose computer with the instructions/code stored thereon. These instructions might take the form of executable code, which is executable by the computer system 600 and/or might take the form of source and/or installable code, which, upon compilation and/or installation on the computer system 600 (e.g., using any of a variety of generally available compilers, installation programs, compression/decompression utilities, etc.), then takes the form of executable code.

It will be apparent to those skilled in the art that substantial variations may be made in accordance with specific requirements. For example, customized hardware might also be used, and/or particular elements might be implemented in hardware, software (including portable software, such as applets, etc.), or both. Further, connection to other computing devices such as network input/output devices may be employed.

In one aspect, the invention employs a computer system (such as the computer system 600) to perform methods of the invention. According to a set of embodiments, some or all of the procedures of such methods are performed by the computer system 600 in response to processor(s) 610 executing one or more sequences of one or more instructions (which might be incorporated into the operating system 640 and/or other code, such as an application program 645) contained in the working memory 635. Such instructions may be read into the working memory 635 from another machine-readable medium, such as one or more of the storage device(s) 625. Merely by way of example, execution of the sequences of instructions contained in the working memory 635 might cause the processor(s) 610 to perform one or more procedures of the methods described herein.

The terms "machine-readable medium" and "computer readable medium," as used herein, refer to any medium that participates in providing data that causes a machine to operate in a specific fashion. In an embodiment implemented using the computer system 600, various machine-readable media might be involved in providing instructions/code to processor(s) 610 for execution and/or might be used to store and/or carry such instructions/code (e.g., as signals). In many implementations, a computer-readable medium is a physical and/or tangible storage medium. Such a medium may take many forms, including but not limited to, non-volatile media, volatile media, and transmission media. Non-volatile media may include, for example, optical or magnetic disks, such as the storage device(s) 625. Volatile media may include, without limitation, dynamic memory, such as the working memory 635. Transmission media may include coaxial cables, copper wire and fiber optics, including the wires that comprise the bus 605, as well as the various components of the communications subsystem 630 (and/or the media by which the communications subsystem 630 provides communication with other devices). Hence, transmission media can also take the form of waves (including without limitation radio, acoustic and/or light waves, such as those generated during radio wave and infrared data communications).

Common forms of physical and/or tangible computer-readable media include, for example, a floppy disk, a flexible disk, a hard disk, magnetic tape, or any other magnetic medium, a CD-ROM, any other optical medium, punchcards, papertape, any other physical medium with patterns of holes, a RAM, a PROM, an EPROM, a FLASH-EPROM, any other memory chip or cartridge, a carrier wave as described hereinafter, or any other medium from which a computer can read instructions and/or code.

Various forms of machine-readable media may be involved in carrying one or more sequences of one or more instructions to the processor(s) 610 for execution. Merely by way of example, the instructions may initially be carried on a magnetic disk and/or optical disc of a remote computer. A remote computer might load the instructions into its dynamic memory and send the instructions as signals over a transmission medium to be received and/or executed by the computer system 600. These signals, which might be in the form of electromagnetic signals, acoustic signals, optical signals and/and/or the like, are all examples of carrier waves on which instructions can be encoded, in accordance with various embodiments of the invention.

The communications subsystem 630 (and/or components thereof) generally will receive the signals, and the bus 605 then might carry the signals (and/or the data, instructions, etc., carried by the signals) to the working memory 635, from which the processor(s) 610 retrieves and executes the instructions. The instructions received by the working memory 635 may optionally be stored on a storage device 625 either before or after execution by the processor(s) 610.

Figure 7:
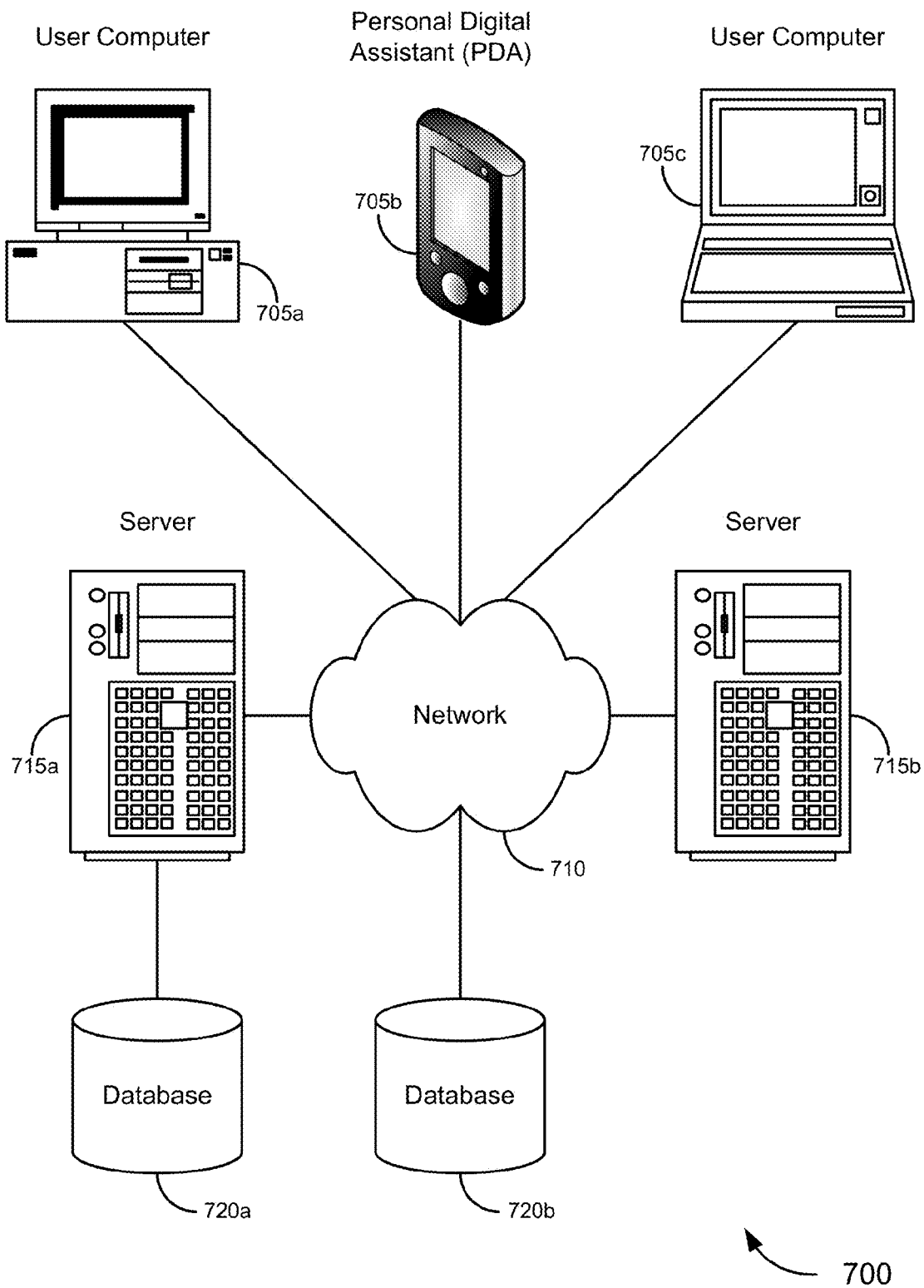
FIG. 7 is a block diagram illustrating a networked system of computers for implementing aspects of the present invention.

Merely by way of example, FIG. 7 illustrates a schematic diagram of a system 700 that can be used in accordance with one set of embodiments. The system 700 can include one or more user computers 705. The user computers 705 can be general purpose personal computers (including, merely by way of example, personal computers, tablet computers, and/or laptop computers running any appropriate flavor of Microsoft Corp.'s Windows™ and/or Apple Corp.'s Macintosh™ operating systems) and/or workstation computers running any of a variety of commercially available UNIX™ or UNIX-like operating systems. These user computers 705 can also have any of a variety of applications, including one or more applications configured to perform methods of the invention, as well as one or more office applications, database client and/or server applications, and web browser applications. Alternatively, the user computers 705 can be any other electronic device, such as a thin-client computer, Internet-enabled mobile telephone, smart phone, cellular phone, digital music player, and/or personal digital assistant (PDA), capable of communicating via a network (e.g., the network 710 described below) and/or displaying and navigating web pages or other types of electronic documents. Although the exemplary system 700 is shown with three user computers 705, any number of user computers can be supported.

Certain embodiments of the invention operate in a networked environment, which can include a network 710. The network 710 can be any type of network familiar to those skilled in the art that can support data communications using any of a variety of commercially available protocols, including without limitation TCP/IP, SNA, IPX, AppleTalk, and the like. Merely by way of example, the network 710 can be a local area network ("LAN"), including without limitation an Ethernet network, a Token-Ring network and/or the like; a wide-area network (WAN); a virtual network, including without limitation a virtual private network ("VPN"); the Internet; an intranet; an extranet; a public switched telephone network ("PSTN"); an infrared network; a wireless network, including without limitation a network operating under any of the IEEE 802.11 suite of protocols, the Bluetooth™ protocol known in the art, and/or any other wireless protocol; and/or any combination of these and/or other networks.

Embodiments of the invention can include one or more server computers 715. Each of the server computers 715 may be configured with an operating system, including without limitation any of those discussed above, as well as any commercially (or freely) available server operating systems. Each of the servers 715 may also be running one or more applications, which can be configured to provide services to one or more clients 705 and/or other servers 715.

Merely by way of example, one of the servers 715 may be a web server, which can be used, merely by way of example, to process requests for web pages or other electronic documents from user computers 705. The web server can also run a variety of server applications, including HTTP servers, FTP servers, CGI servers, database servers, Java™ servers, and the like. In some embodiments of the invention, the web server may be configured to serve web pages that can be operated within a web browser on one or more of the user computers 705 to perform methods of the invention.

The server computers 715, in some embodiments, might include one or more application servers, which can include one or more applications accessible by a client running on one or more of the client computers 705 and/or other servers 715. Merely by way of example, the server(s) 715 can be one or more general purpose computers capable of executing programs or scripts in response to the user computers 705 and/or other servers 715, including without limitation web applications (which might, in some cases, be configured to perform methods of the invention). Merely by way of example, a web application can be implemented as one or more scripts or programs written in any suitable programming language, such as Java™, C, C#™ or C++, and/or any scripting language, such as Perl, Python, Ruby, or TCL, as well as combinations of any programming/scripting languages. The application server(s) can also include database servers, including without limitation those commercially available from Oracle™, Microsoft™, Sybase™, IBM™ and the like, which can process requests from clients (including, depending on the configuration, database clients, API clients, web browsers, etc.) running on a user computer 705 and/or another server 715. In some embodiments, an application server can create web pages dynamically for displaying the information in accordance with embodiments of the invention. Data provided by an application server may be formatted as web pages (comprising HTML, JavaScript, etc., for example) and/or may be forwarded to a user computer 705 via a web server (as described above, for example). Similarly, a web server might receive web page requests and/or input data from a user computer 705 and/or forward the web page requests and/or input data to an application server. In some cases a web server may be integrated with an application server.

In accordance with further embodiments, one or more servers 715 can function as a file server and/or can include one or more of the files (e.g., application code, data files, etc.) necessary to implement methods of the invention incorporated by an application running on a user computer 705 and/or another server 715. Alternatively, as those skilled in the art will appreciate, a file server can include all necessary files, allowing such an application to be invoked remotely by a user computer 705 and/or server 715. It should be noted that the functions described with respect to various servers herein (e.g., application server, database server, web server, file server, etc.) can be performed by a single server and/or a plurality of specialized servers, depending on implementation-specific needs and parameters.

In certain embodiments, the system can include one or more databases 720. The location of the database(s) 720 is discretionary. Merely by way of example, a database 720a might reside on a storage medium local to (and/or resident in) a server 715a (and/or a user computer 705). Alternatively, a database 720b can be remote from any or all of the computers 705, 715, so long as the database can be in communication (e.g., via the network 710) with one or more of these. In a particular set of embodiments, a database 720 can reside in a storage-area network ("SAN") familiar to those skilled in the art. (Likewise, any necessary files for performing the functions attributed to the computers 705, 715 can be stored locally on the respective computer and/or remotely, as appropriate.) In one set of embodiments, the database 720 can be a relational database, such as an Oracle™ database, that is adapted to store, update, and retrieve data in response to SQL-formatted commands. The database might be controlled and/or maintained by a database server, as described above, for example.

It should be noted that the methods, systems, and devices discussed above are intended merely to be examples. It must be stressed that various embodiments may omit, substitute, or add various procedures or components as appropriate. For instance, it should be appreciated that, in alternative embodiments, the methods may be performed in an order different from that described, and that various steps may be added, omitted, or combined. Also, features described with respect to certain embodiments may be combined in various other embodiments. Different aspects and elements of the embodiments may be combined in a similar manner. Also, it should be emphasized that technology evolves and, thus, many of the elements are examples and should not be interpreted to limit the scope of the invention.

Specific details are given in the description to provide a thorough understanding of the embodiments. However, it will be understood by one of ordinary skill in the art that the embodiments may be practiced without these specific details. For example, well-known circuits, processes, algorithms, structures, and techniques have been shown without unnecessary detail in order to avoid obscuring the embodiments. This description provides example embodiments only, and is not intended to limit the scope, applicability, or configuration of the invention. Rather, the preceding description of the embodiments will provide those skilled in the art with an enabling description for implementing embodiments of the invention. Various changes may be made in the function and arrangement of elements without departing from the spirit and scope of the invention.

Also, it is noted that the embodiments may be described as a process that is depicted as a flow diagram or block diagram. Although each may describe the operations as a sequential process, many of the operations can be performed in parallel or concurrently. In addition, the order of the operations may be rearranged. A process may have additional steps not included in the figure. Furthermore, embodiments of the methods may be implemented by hardware, software, firmware, middleware, microcode, hardware description languages, or any combination thereof. When implemented in software, firmware, middleware, or microcode, the program code or code segments to perform the necessary tasks may be stored in a computer-readable medium such as a storage medium. Processors may perform the necessary tasks.

Having described several embodiments, it will be recognized by those of skill in the art that various modifications, alternative constructions, and equivalents may be used without departing from the spirit of the invention. For example, the above elements may merely be a component of a larger system, wherein other rules may take precedence over or otherwise modify the application of the invention. Also, a number of steps may be undertaken before, during, or after the above elements are considered. Accordingly, the above description should not be taken as limiting the scope of the invention.

What is claimed is:

1. A method for navigating between a plurality of genealogical records, displayed on a touch-screen device, the method comprising:
receiving a selection of a first genealogical record in the plurality of genealogical records;
determining a plurality of familial records in the plurality of genealogical records that are related to the first genealogical record through one or more familial lines;
determining a first display group comprised of the first genealogical record and a familial record in the one or more familial lines;
determining a second display group comprises of a second familial record in a first familial line, wherein the second familial record in the second display group sequentially follows a familial record in the first display group;
causing to be displayed on a touch screen of the touch-screen device, a first plurality of icons representing each familial record in the first display group, wherein each icon in the first plurality of icons is positioned according to the one or more familial lines such that each familial line forms a familial line direction, the first plurality of icons arranged in at least two sections defined by a dividing line;
determining a direction from a finger gesture input from the touch screen of the touch-screen device;
determining that one of the one or more familial lines corresponds to the direction of the finger gesture input;
adding to the first display group, the second familial record from the second display group;
adding to the second display group, a paternal familial record in the first familial line that follows after the second familial record in the second display group;
adding to the second display group, a maternal record in a second familial line that follows after the second familial record in the second display group;
causing to be displayed on the touch screen of the touch-screen device, an icon representing the paternal familial record added to the first display group when the finger gesture input begins in a first section of the at least two sections; and
causing to be displayed on the touch screen of the touch-screen device, an icon representing the maternal familial record added to the first display group when the finger gesture input begins in a second section of the at least two sections.

2. The method for navigating between a plurality of genealogical records displayed on a touch-screen device of claim 1 further comprising:
  storing the plurality of genealogical records in a memory;
  storing display information for the first display group in a cache memory; and
  storing display information for the second display group in the cache memory.

3. The method for navigating between a plurality of genealogical records displayed on a touch-screen device of claim 1 further comprising removing from the first display group and the second display group, any familial records that are not a part of the first familial line.

4. The method for navigating between a plurality of genealogical records displayed on a touch-screen device of claim 1, wherein the first display group comprises parents and grandparents of the first genealogical record.

5. The method for navigating between a plurality of genealogical records displayed on a touch-screen device of claim 4, wherein the first display group further comprises children and siblings of the first genealogical record.

6. The method for navigating between a plurality of genealogical records displayed on a touch-screen device of claim 1, wherein the second familial record is associated with a great-grandparent of the first genealogical record.

7. The method for navigating between a plurality of genealogical records displayed on a touch-screen device of claim 1, wherein a number of familial records in the first display group is determined based on a size of the touch screen and an amount of information available for each familial record.

8. A system for displaying and navigating between a plurality of genealogical records, the system comprising:
  a processor;
  a touch screen; and
  a storage memory coupled with the processor, the storage memory including a set of instructions stored thereon which, when executed by the processor, cause the processor to:
  store the plurality of genealogical records;
  receive a selection of a first genealogical record in the plurality of genealogical records;
  determine a plurality of familial records in the plurality of genealogical records that are related to the first genealogical record through one or more familial lines;
  determine a first display group comprised of the first genealogical record and a familial record in the one or more familial lines;
  determine a second display group comprises of a second familial record in a first familial line, wherein the second familial record in the second display group sequentially follows a familial record in the first display group;
  cause to be displayed on a touch screen, a first plurality of icons representing each familial record in the first display group, wherein each icon in the first plurality of icons is positioned according to the one or more familial lines such that each familial line forms a familial line direction, the first plurality of icons arranged in at least two sections defined by a dividing line;
  determine a direction from a finger gesture input from the touch screen;
  determine that one of the one or more familial lines corresponds to the direction of the finger gesture input;
  add to the first display group, the second familial record from the second display group;
  add to the second display group, a paternal familial record in the first familial line that follows after the second familial record in the second display group;
  add to the second display group, a maternal record in a second familial line that follows after the second familial record in the second display group;
  cause to be displayed on the touch screen, an icon representing the paternal familial record added to the first display group when the finger gesture input begins in a first section of the at least two sections; and
  cause to be displayed on the touch screen, an icon representing the maternal familial record added to the first display group when the finger gesture input begins in a second section of the at least two sections.

9. The system for displaying and navigating between a plurality of genealogical records of claim 8, wherein the instructions further cause the processor to:
  receive a second finger gesture input from the touch screen;
  determine a vertical component of the second finger gesture input; and
  using the vertical component of the second finger gesture input, select a child of the first genealogical record.

10. The system for displaying and navigating between a plurality of genealogical records of claim 8, wherein the at least two sections are arranged vertically.

11. The system for displaying and navigating between a plurality of genealogical records of claim 8, wherein when the processor causes to be displayed on the touch screen an icon representing the second familial record, comprising a continuous animation such that a set of relationships between familial records in the first display group are visually maintained.

12. The system for displaying and navigating between a plurality of genealogical records of claim 8, wherein causing the first plurality of icons to be displayed on the touch screen comprises:
  providing a docking field configured to receive an icon for the first genealogical record; and
  positioning icons representing each familial record in the first display group relative to the docking field according to a type of familial relationship between each familial record and the first genealogical record.

13. The system for displaying and navigating between a plurality of genealogical records of claim 12, wherein the set of instructions further causes the processor to determine the direction of a zoom command from a second finger gesture input from the touch screen, and change the first display group according to the direction of the zoom command.

14. The system for displaying and navigating between a plurality of genealogical records of claim 12, the instructions further cause the processor to move a next icon in the first familial line in the direction of the finger gesture input into the docking field.

15. The method of claim 1, wherein determining a direction from a finger gesture input comprises determining directional components from the finger gesture input, and wherein determining that one of the one or more familial lines corresponds to the direction of the finger gesture input comprises determining that one of the directional components of the finger gesture input corresponds to the familial line direction of one of the one or more familial lines.

16. The method of claim 15, wherein causing to be displayed on the touch screen an icon representing the second familial record comprises:
  adding display content on the touch screen in a display direction in order to include the second familial record, based on the familial line direction of the first familial line.

17. The method of claim 16, wherein the display direction of adding content is in the direction of the first familial line, and wherein the magnitude of the added display content in the direction of the first familial line is proportional to the magnitude of the directional component of the finger gesture input corresponding to the familial line direction of the first familial line.

18. The method of claim 16, wherein the display direction of adding content is further based on the starting point of the finger gesture input on the touch screen.

19. A method for navigating between a plurality of genealogical records displayed on a touch-screen device, the method comprising:
- receiving a selection of a first genealogical record in the plurality of genealogical records;
- determining a plurality of familial records in the plurality of genealogical records that are related to the first genealogical record through one or more familial lines;
- determining a first display group comprising the first genealogical record and a familial record in the one or more familial lines;
- determining a second display group comprising a paternal familial record in a first familial line, wherein the paternal familial record in the second display group sequentially follows a familial record in the first display group;
- determining a third display group comprising a maternal familial record in a second familial line, wherein the maternal familial record in the third display group sequentially follows a familial record in the first display group;
- causing to be displayed on a touch screen of the touch-screen device, a first plurality of icons representing each familial record in the first display group, wherein each icon in the first plurality of icons is positioned according to the one or more familial lines such that each familial line forms a familial line direction, the first plurality of icons arranged in at least two sections defined by a dividing line;
- determining a direction from a finger gesture input from the touch screen of the touch-screen device;
- determining that one of the one or more familial lines corresponds to the direction of the finger gesture input;
- causing to be displayed on the touch screen of the touch-screen device, an icon representing the paternal familial record added to the first display group when the finger gesture input begins in one of the two sections; and
- causing to be displayed on the touch screen of the touch-screen device, an icon representing the maternal familial record added to the first display group when the finger gesture input begins in the other of the two sections.

* * * * *